(12) United States Patent
Salem

(10) Patent No.: US 12,165,544 B2
(45) Date of Patent: *Dec. 10, 2024

(54) DRONE APPARATUS USED IN HEALTHCARE APPLICATIONS

(71) Applicant: Mores, Inc., Burbank, CA (US)

(72) Inventor: Ayman Salem, Burbank, CA (US)

(73) Assignee: Mores, Inc., Toluca Lake, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/861,616

(22) Filed: Jul. 11, 2022

(65) Prior Publication Data

US 2024/0078940 A1 Mar. 7, 2024

Related U.S. Application Data

(63) Continuation of application No. 16/776,410, filed on Jan. 29, 2020, now Pat. No. 11,386,818, which is a
(Continued)

(51) Int. Cl.
*G09F 21/12* (2006.01)
*B60L 53/60* (2019.01)
(Continued)

(52) U.S. Cl.
CPC ............... *G09F 21/12* (2013.01); *B64B 1/58* (2013.01); *B64C 39/024* (2013.01); *G05D 1/104* (2013.01);
(Continued)

(58) Field of Classification Search
CPC ........... G09F 21/12; G05D 1/104; B64B 1/58; B64C 39/024; B64C 2201/12; B64C 2201/027; B64C 2201/042; B64C 2201/101; B64C 2201/108; B64C 2201/128; B64C 2201/143; Y02T 90/12; Y02T 90/14; Y02T 90/16; Y02T 10/7072; B60L 2200/10; B60L 53/60; B64F 1/362; B64U 10/13; B64U 10/30; B64U 30/20;
(Continued)

(56) References Cited

U.S. PATENT DOCUMENTS

| 8,948,935 | B1* | 2/2015 | Peeters | G05D 1/102 |
| | | | | 709/201 |
| 9,307,383 | B1* | 4/2016 | Patrick | B64U 10/14 |

(Continued)

*Primary Examiner* — Russell Frejd
(74) *Attorney, Agent, or Firm* — Smyrski Patent Law PC

(57) ABSTRACT

A system including a drone device comprising securable compartments, each of the securable compartments lockable and configured to be unlocked by a user or a remote device is provided. The system also includes a series of sensors provided with the drone device and configured to assess health attributes of the user while the drone is positioned proximate the user and a remote computing system configured to receive sensed information from the drone device and assess health of the user, wherein the remote computing system holographically displays health attributes of the user. The drone device travels to the user to provide or receive healthcare related objects to or from the user. The series of sensors comprise at least one audio sensor and at least one video sensor configured to assess user health attributes about the user's body in a contactless manner based on both audio and visual health attribute readings.

20 Claims, 23 Drawing Sheets

Related U.S. Application Data continuation-in-part of application No. 16/578,133, filed on Sep. 20, 2019, now Pat. No. 11,014,467, which is a continuation of application No. 15/162,381, filed on May 23, 2016, now Pat. No. 10,424,231, said application No. 16/776,410 is a continuation-in-part of application No. 16/027,352, filed on Jul. 4, 2018, and a continuation-in-part of application No. 15/943,585, filed on Apr. 2, 2018, which is a continuation-in-part of application No. 15/797,650, filed on Oct. 30, 2017, now abandoned, which is a continuation-in-part of application No. 14/952,424, filed on Nov. 25, 2015, now Pat. No. 9,838,508, which is a continuation-in-part of application No. 14/080,021, filed on Nov. 14, 2013, now Pat. No. 9,747,417.

(51) Int. Cl.

| | | |
|---|---|---|
| *B64B 1/58* | (2006.01) | |
| *B64C 39/02* | (2023.01) | |
| *B64U 10/13* | (2023.01) | |
| *B64U 10/30* | (2023.01) | |
| *B64U 30/20* | (2023.01) | |
| *B64U 50/19* | (2023.01) | |
| *B64U 101/00* | (2023.01) | |
| *B64U 101/60* | (2023.01) | |
| *G05D 1/00* | (2024.01) | |

(52) U.S. Cl.
CPC ........... *B60L 53/60* (2019.02); *B60L 2200/10* (2013.01); *B64U 10/13* (2023.01); *B64U 10/30* (2023.01); *B64U 30/20* (2023.01); *B64U 50/19* (2023.01); *B64U 2101/00* (2023.01); *B64U 2101/60* (2023.01); *B64U 2201/102* (2023.01); *Y02T 10/7072* (2013.01); *Y02T 90/12* (2013.01); *Y02T 90/14* (2013.01); *Y02T 90/16* (2013.01)

(58) Field of Classification Search
CPC   B64U 50/19; B64U 2101/00; B64U 2101/60; B64U 2101/102
See application file for complete search history.

(56) References Cited

U.S. PATENT DOCUMENTS

| | | | |
|---|---|---|---|
| 9,552,056 B1* | 1/2017 | Barry | B25J 9/1689 |
| 2006/0154642 A1* | 7/2006 | Scannell | G08B 7/066 |
| | | | 455/404.1 |
| 2009/0050750 A1* | 2/2009 | Goossen | B64D 1/22 |
| | | | 901/14 |
| 2010/0308999 A1* | 12/2010 | Chornenky | G08B 6/00 |
| | | | 700/245 |
| 2011/0130636 A1* | 6/2011 | Daniel | H04Q 9/00 |
| | | | 709/201 |

* cited by examiner

DRONE APPARATUS USED IN HEALTHCARE APPLICATIONS

The present application is a continuation of co-pending U.S. patent application Ser. No. 16/776,410, entitled "Drone Apparatus Used in Healthcare Applications," inventor Ayman Salem, filed Jan. 29, 2020, now U.S. Pat. No. 11,386,818, which is a continuation-in-part of U.S. patent application Ser. No. 16/578,133, entitled "Self Charging Lightweight Drone Apparatus," inventor Ayman Salem, filed Sep. 20, 2019, now U.S. Pat. No. 11,014,467, which is a continuation of U.S. patent application Ser. No. 15/162,381, entitled "Self Charging Lightweight Drone Apparatus," inventor Ayman Salem, filed May 23, 2016, now. U.S. Pat. No. 10,424,231, which claims priority based on U.S. Provisional Patent Application Ser. No. 61/166,629, entitled "Self Charging Lightweight Drone Apparatus," inventor Ayman Salem, filed May 25, 2015.

Co-pending U.S. patent application Ser. No. 16/776,410, now U.S. Pat. No. 11,386,818, is also a continuation-in-part of U.S. patent application Ser. No. 16/027,352, entitled "System for Remote Noninvasive Contactless Assessment and Prediction of Body Organ Health," inventor Ayman Salem, filed Jul. 4, 2018.

Co-pending U.S. patent application Ser. No. 16/776,410, now U.S. Pat. No. 11,386,818, is further a continuation-in-part of U.S. patent application Ser. No. 15/943,585, entitled "Enhanced Personal Care System Employing Blockchain Functionality," inventor Ayman Salem, filed Apr. 2, 2018, which is a continuation-in-part of U.S. patent application Ser. No. 15/797,650, entitled "Method and Apparatus for Enhanced Personal Care with Interactive Diary," inventor Ayman Salem, filed Oct. 30, 2017, which is a continuation of U.S. patent application Ser. No. 14/952,424, entitled "Method and Apparatus for Enhanced Personal Care with Interactive Diary," inventor Ayman Salem, filed Nov. 25, 2015, now U.S. Pat. No. 9,838,508, which is a continuation-in-part of U.S. patent application Ser. No. 14/080,021, inventor Ayman Salem, entitled "Method and Apparatus for Enhanced Personal Care," filed Nov. 14, 2013, now U.S. Pat. No. 9,747,417.

All of the foregoing are incorporated herein by reference in their entireties.

BACKGROUND OF THE INVENTION

Field of the Invention

The present invention relates in general to aerodynamic devices, and more specifically a drone arrangement useable in healthcare applications.

Description of the Related Art

Ongoing needs exist for lightweight and readily deployable devices that can accomplish certain healthcare tasks. Many consumers and patients are in remote areas and/or have little access to transportation and/or appropriate medical facilities. Such patients may not receive the medical care needed or may only receive a certain level of care depending on available facilities.

Certain ways of addressing this have been explored. For example, mobile healthcare vehicles have been employed, at significant cost and with limited capacities. For example, it is difficult to provide extensive, heavy, or complex medical equipment on such devices. Further, they require travel time for physicians and/or clinicians, and such travel is time when these individuals are not seeing patients.

Services such as mail or other delivery options have been employed. In this scenario, the patient may take a noninvasive sample, such as saliva, and may mail the sample to a lab for analysis. Problems with this method include an inability to do a broad assessment, as the samples available from a patient tend to be limited, and can get contaminated or lose attributes over time, and thus can be highly limited. Patients can also perform procedures on themselves, such as checking heart rate, temperature, weight, and so forth, but again, these can be fairly limited.

Thus there is a need for assessing patients and collecting samples for evaluation, potentially benefitting patients without transportation and relatively distant from appropriate medical facilities, that addresses issues associated with previous designs.

SUMMARY OF THE INVENTION

According to one embodiment of the present design, there is provided a system comprising a drone device comprising a plurality of securable compartments, each of the securable compartments lockable and configured to be unlocked by a user or a remote device, wherein the user comprises a user approved to unlock at least one locking compartment, a series of sensors provided with the drone device and configured to assess health attributes of the user while the drone is positioned proximate the user, and a remote computing system configured to receive sensed information from the drone device and assess health of the user, wherein the remote computing system holographically displays health attributes of the user. The drone device travels to the user to provide or receive healthcare related objects to or from the user, and the series of sensors comprise at least one audio sensor and at least one video sensor jointly configured to assess user health attributes about the user's body in a contactless manner based on both audio and visual health attribute readings, wherein the contactless manner comprises refraining from physically contacting the user's body.

According to another embodiment of the present design, there is provided a rechargeable drone device arrangement comprising a series of sensors configured to receive information about a user and transmit the information to a computing system configured to assess the information collected from the drone device, a plurality of locking securable compartments configured to maintain samples or medications, wherein the plurality of locking securable compartments are each configured to be openable only by an approved individual, and a remote computing system configured to receive sensed information from the drone device and assess health of the user, wherein the remote computing system holographically displays health attributes of the user. The drone device travels to the user to provide or receive healthcare related objects to or from the user. The series of sensors comprise at least one audio sensor and at least one video sensor jointly configured to assess user health attributes about the user's body in a contactless manner using both audio and visual health attribute readings, wherein the contactless manner comprises refraining from physically contacting the user's body.

According to a further embodiment of the present design, there is provided a system comprising a drone device comprising a plurality of locking securable compartments, each of the plurality of locking securable compartments configured to be unlocked only by a user or a remote device, wherein the user comprises a user approved to unlock at least one locking securable compartment, and a series of sensors configured to assess health attributes of the user while the drone is positioned proximate the user, wherein the series of sensors comprise at least one audio sensor and at least one video sensor configured to assess user health attributes about the user's body in a contactless manner based on both audio and visual health attribute readings, wherein the contactless manner comprises refraining from physically contacting the user's body, and a remote computing system configured to receive sensed information from the drone device and assess health of the user, wherein the remote computing system holographically displays health attributes of the user. The drone device travels to the user to provide or receive healthcare related objects to or from the user.

These and other advantages of the present invention will become apparent to those skilled in the art from the following detailed description of the invention and the accompanying drawings.

BRIEF DESCRIPTION OF THE DRAWINGS

For a more complete understanding of the present disclosure, reference is now made to the following figures, wherein like reference numbers refer to similar items throughout the figures.

Figure 1:
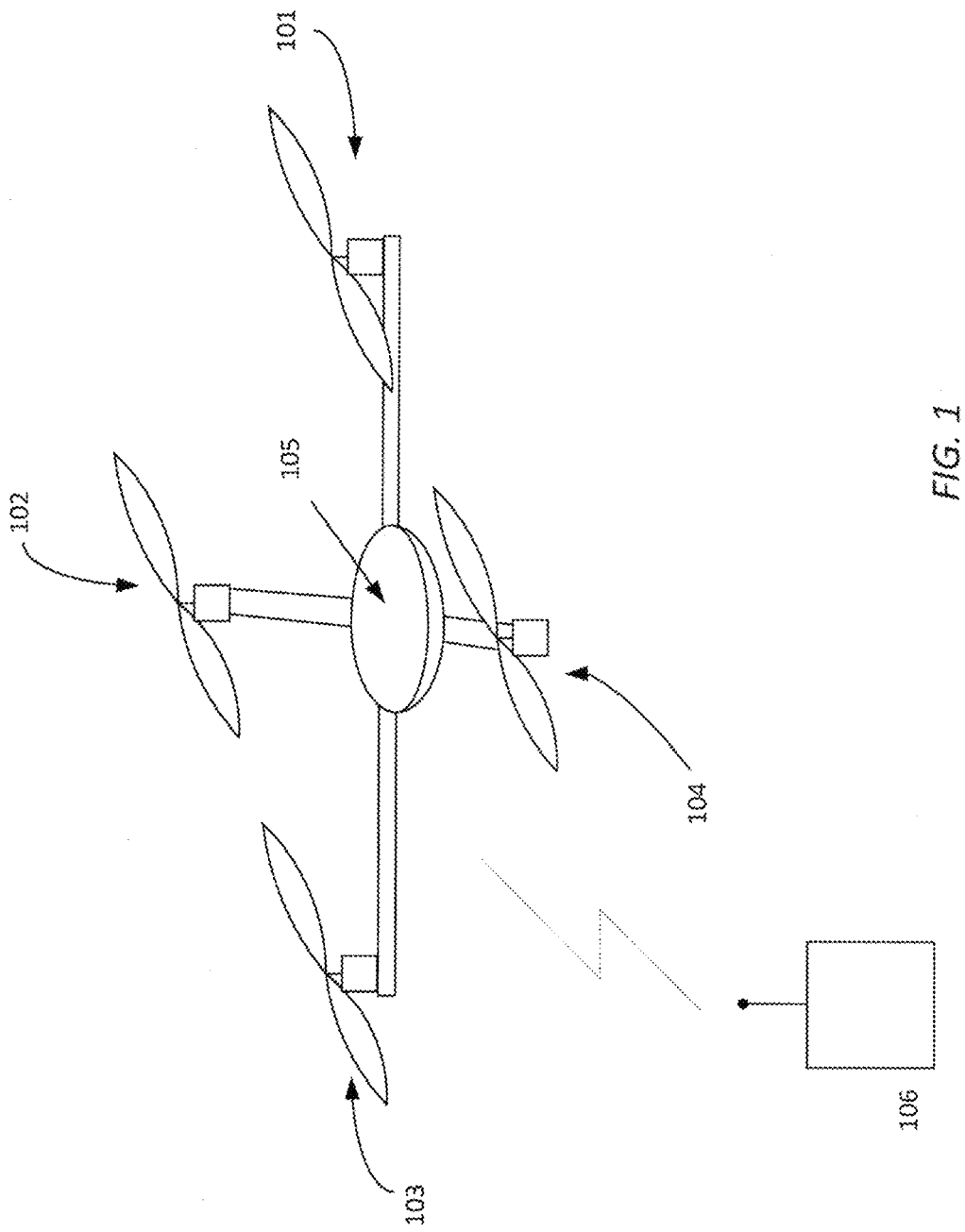
FIG. 1 illustrates one type of drone device or apparatus.

The exemplification set out herein illustrates particular embodiments, and such exemplification is not intended to be construed as limiting in any manner.

DETAILED DESCRIPTION OF THE INVENTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

In general, the present invention includes a drone device arrangement or a system including a variety of drone devices able to be deployed to or toward a patient for the express purpose of assessing the patient and/or receiving samples and returning the samples to a testing facility, hospital, or other appropriate collection site. In one embodiment, the drone device includes collection hardware, including an opening with hardware located therein that can be retrieved and filled and may be spring loaded, in one embodiment with a digital indicator provided. In another embodiment, a collection of lightweight drones may be provided on a vehicle or a base station, transported to a preferred or desired location, and drones sent to individual patients for assessment and/or collection.

The lightweight drone device arrangement may include a sensor or sensors provided with one or more of the drones, and the lightweight drones may be provided with recharge capability via a charging station or stations. Sensors may be employed to assess the health of the individual in a contactless manner. When sensors are employed, the arrangement can be positioned or repositioned to take advantage of a certain situation, such as positioning close to a target. Sensors to evaluate patient condition and health may be employed, including but not limited to cameras or microphones. Contactless sensing of a person's health attributes may also be employed as discussed herein.

Drones are devices that can be flown without a pilot and have been used extensively in military and more recently in civilian activities. Drones are typically controllable by a user or a controller from a distance. Different types of drones are available, and certain drones may include different arrangements, numbers of propellers and/or propelling sources, and may vary in size. However, due to the requirements of a drone in the Earth's atmosphere, such devices must be relatively light and their propellant sources relatively powerful.

The present disclosure uses the term "drone arrangement" to mean a collection of one or more drones and use of the word "drone" or "drone arrangement" is intended broadly. The term "micro drone" is intended to represent a small drone and is not intended to be limiting and use of terms such as "drone" and "micro drone" are not intended to be limiting as to size of the device, and in some instances may be used interchangeably. The term "drone" as used herein mean any type of hovering unmanned propelled device irrespective of size. The term "drone arrangement" is generally employed to cover any of the designs suggested herein or any similar type of device, apparatus, system, or arrangement.

A drawing of one type of drone is presented in FIG. 1. From FIG. 1, the drone 100 includes four upward facing propellers 101-104 that rotate and provide lift, and the propellers 101-104 are electrically connected to a central controller 105 positioned in the center of the drone 100. A remote device 106 is typically provided that can provide commands, such as increase lift, decrease lift in order to hover, or move in a given direction. The central controller 105 may include a printed circuit board or other electronics configured to provide control to the drone 100, as well as a power source and a receiver configured to receive signals from a remote transmitter within remote device 106.

In normal operation, a user may move control switches or devices on the remote device 106, which are converted to electronic commands and transmitted to the receiver on the drone 100, which converts the signals received into electronic commands provided to internal electronics that command at least one and as many as all of the propellers to increase or decrease speed. In certain micro drones or drones, an ability to move the axis of rotation of an individual propeller may also be provided and controlled or commanded. Micro drones providing such control ability are commercially available, and any such micro drone or drone, or even a simple hovering and controllable engine, may be employed with the lightweight surface that provides an ability to be controlled to fly in a desired path or course and provide the additional functionality described herein.

While shown with four propellers in FIG. 1, the micro drone may be any sized drone or hovering device and may include any reasonable number of propellers or devices that provide thrust, e.g. aerodynamic thrust, in a fluid such as air, including fewer than four propellers or thrust providing devices or more than four such propellers or thrust providing devices. In essence, any device that can hover, move, and be controlled and can support its weight and additional weight may be employed. Such a device or devices are generically referred to as "drones" or "micro drones" herein, and those terms are intended broadly to include unmanned hovering devices of any shape or form.

The remote device 106 may include different control elements, such as a multi-position switch that allows for sliding right and left and articulating forward and backward. Such controllers and controller switches or control buttons are common in remote control devices such as drones and remote control cars. In the case of drones and micro drones, the buttons may be employed to control throttle, banking, trim, movement direction (left, right, forward, back, up, down, and/or various modes of flight. Movement of the buttons and switches provides control over the drone or micro drone.

Figure 2A:
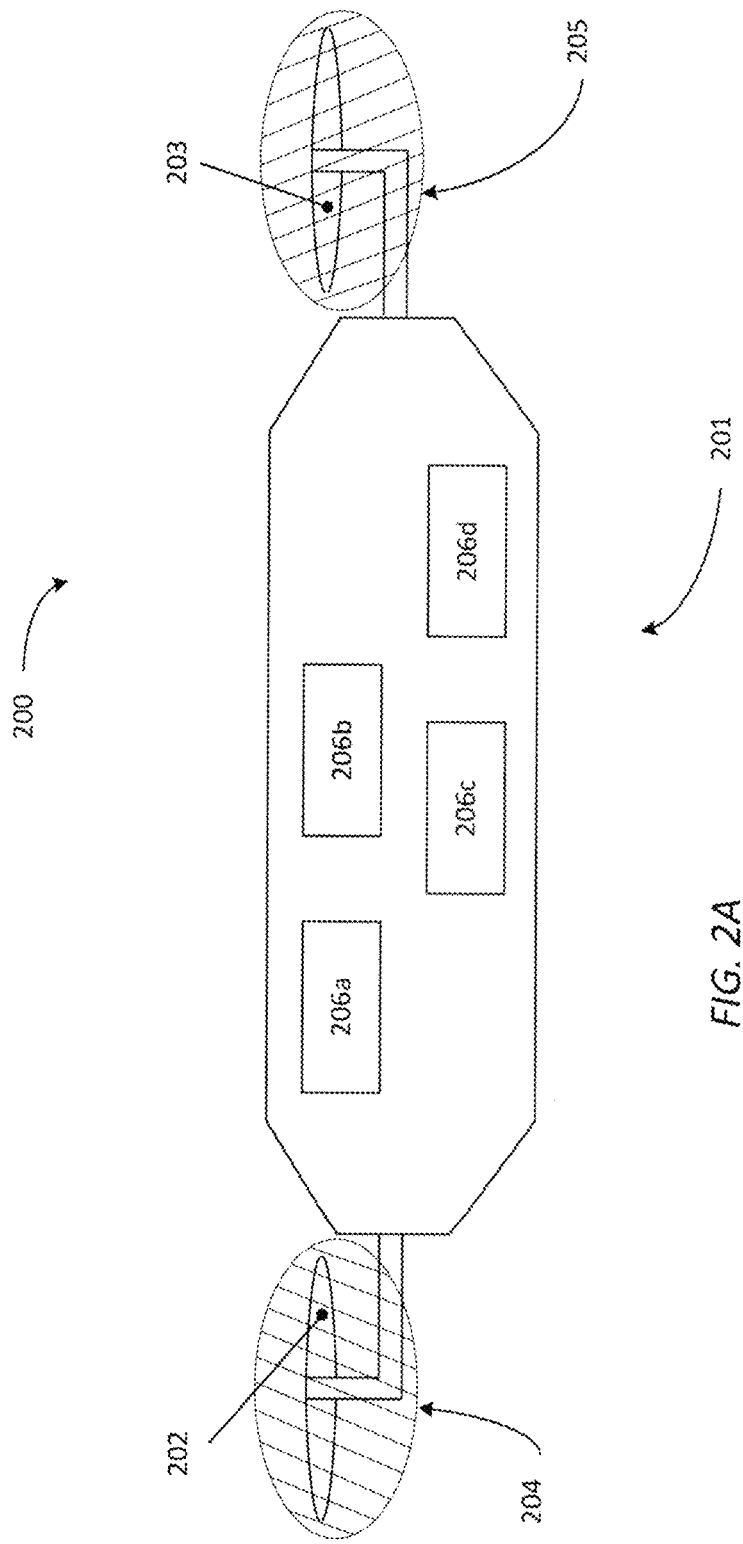
FIG. 2A is an embodiment of a drone device according to the present design.

FIG. 2A shows a first embodiment of a drone according to the present design. From FIG. 2A, drone 200 includes a body 201 and rotors 202 and 203 in this view, representing two rotors of the four employed. Rotor cages 204 and 205 are provided with rotors 202 and 203, respectively, to keep foreign material from fouling the rotors while enabling full thrust. Body 201 comprises a number of bays including a number of trays, in this representation fifteen bays including trays in bays 206a-d. The bays and trays may house items, such as pill prescriptions, or may receive items, such as samples. The front sides of the trays include means to engage or otherwise release the trays such that a user can obtain access. For example, a locking device may be provided wherein a user may have a key, or an electronic code unlockable lock, or a thumbprint reader, retina scanner, combination lock type device, and so forth. In essence, any type of locking mechanism may be employed, and the lock may be remotely operated. For example, when a user wishes to provide a sample to a bay of the drone, and a control unit or person operating a control unit may release the locked bay such that the user can insert the sample. Once unlocked, the opening may be spring loaded such that access to a device such as a carrier or container may be provided to the user.

Figure 2B:
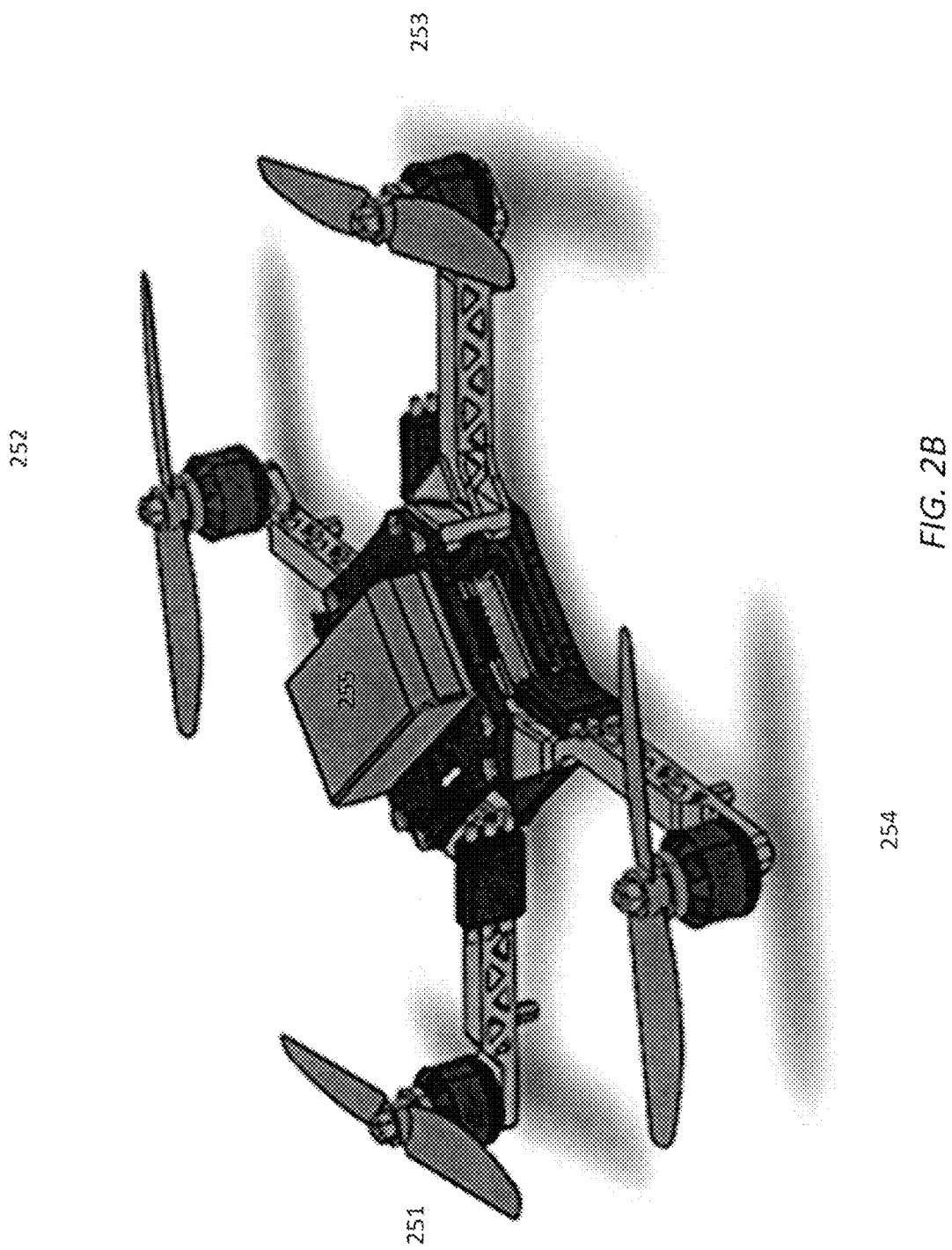
FIG. 2B illustrates an alternate embodiment of a drone according to the present design.

FIG. 2B is an alternate version of a drone according to the present design. Rotors 251-254 are shown, as well as central controller 255.

Figure 3A:
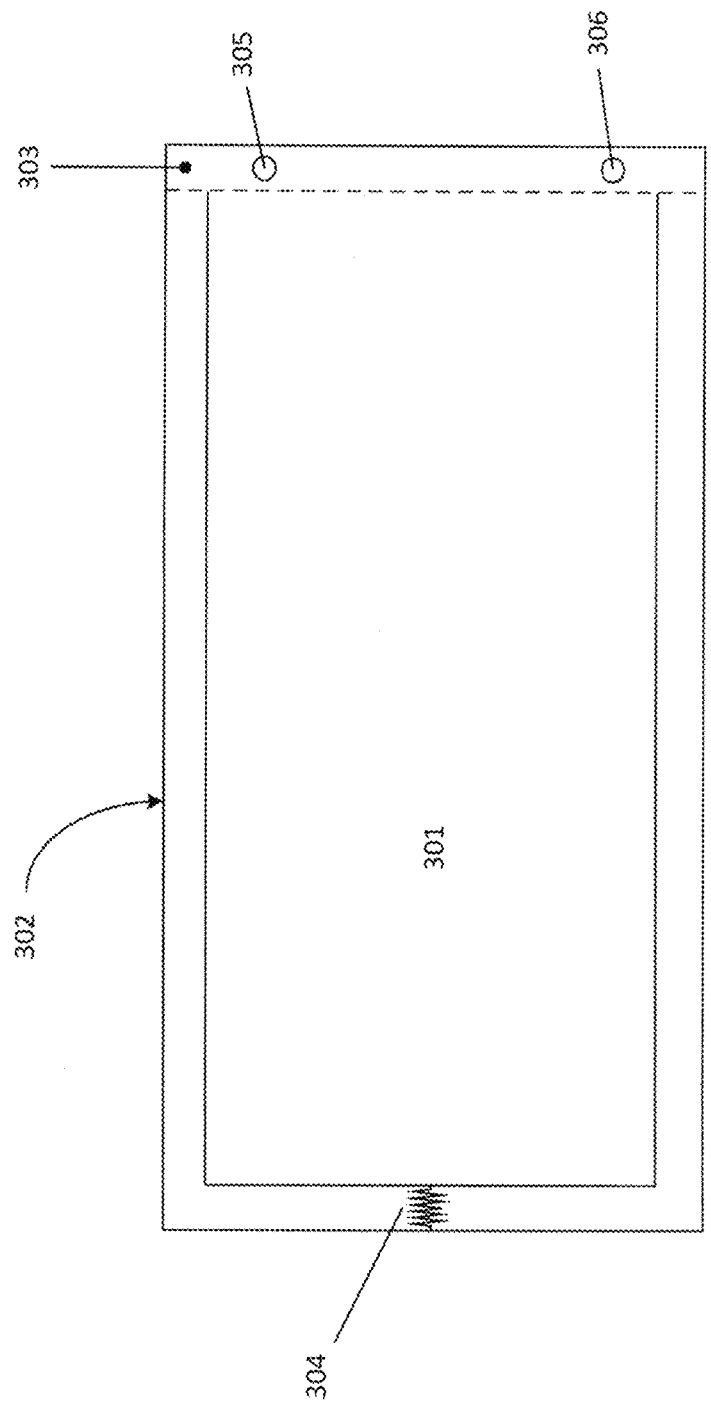
FIG. 3A is a representative side view of a container that may be included in the present design, with the container in a closed position.
Figure 3B:
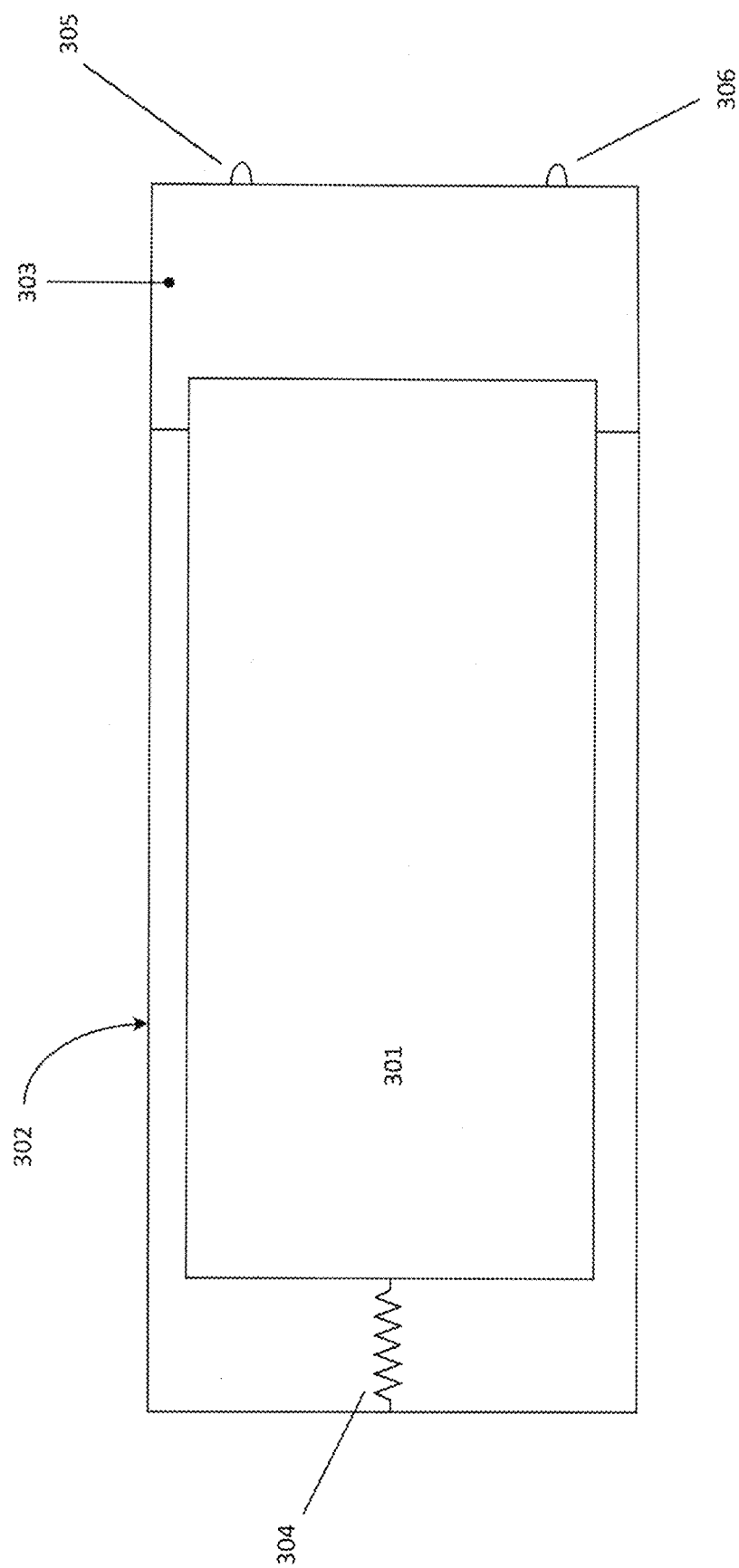
FIG. 3B is a representative side view of a container that may be included in the present design, with the container in an open position.

A representative side view of a container that may be included in the present design is shown in FIGS. 3A and 3B. From FIG. 3A, inner container 301 is held in bay 302 and has front door 303, having two protrusions 305 and 306 locking, in this view, the front door 303 in position and against spring 304. In this arrangement, while protrusions are shown as two circles, in this embodiment these represent two retractable tabs provided at the near edge of front door 303 in this view that engage and lock with an inner wall of bay 302 such that when released, the tabs retract away from the inner wall of bay 302 and allow the front door 303 to swing open. Spring 304 is compressed in this arrangement. The front door 303 has locking and unlocking technology provided therein, such as the options discussed above, and a user or remote device may unlock the front door 303 such as by entering a code by hand or electronically. Once such a code entered or the door locking mechanism is otherwise released, the front door releases the two protrusions 305 and 306, which results in the compressed spring 304 providing force to move the container forward.

FIG. 3B shows the inner container 301 with front door 303 open, here using a hinge (not shown) that either opens front door 303 automatically or allows front door 303 to be opened manually, such as by the user. Spring 304 is decompressed and access is available to the opening of the bay 302. In certain instances, a receptacle sized for the medication or object being provided may be included within the inner container 301, or a receptacle may be provided sized to receive a known object, such as a slide including a sample, a syringe, or other object. Sizing in this manner ensures the appropriate object is received and/or the appropriate medications or objects are provided to the user and lowers the risk of incorrect medical care.

Multiple such containers and bays may be provided with the apparatus, each having separate unlocking hardware, or the opening or door components may be controlled centrally within the drone. For example, the drone may receive a remote command to unlock inner container number six because the drone is known to be proximate patient number six or his/her healthcare provider, and the internal processor in the drone may issue an unlock command to inner container number six.

Figure 4:
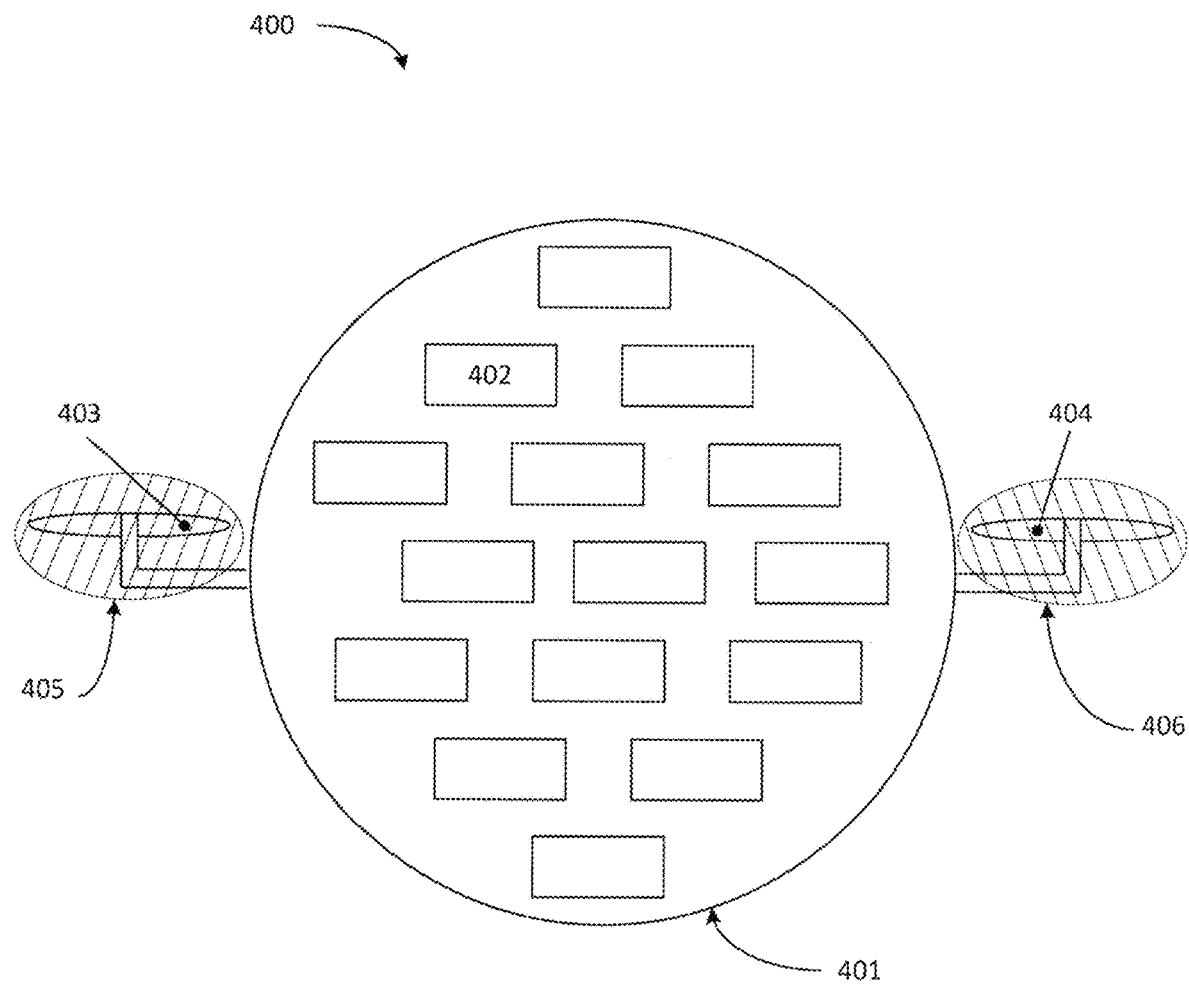
FIG. 4 is an illustration of a drone apparatus employing multiple bays or containers.

FIG. 4 illustrates an arrangement with multiple bays provided with drone 401. FIG. 4 is a side view of the drone 401, including a number of bays such as bay 402. In this configuration, the various bays hold prescriptions, specifically pills, for patients and in this embodiment, each having a digital display provided on the locked door. The digital display may display varying information, such as the name of the patient, a code representing the patient, a reminder or indicator (e.g. "Wednesday dosage"), or other relevant information. In one embodiment, one or more of the bays may be intended to receive a sample from a patient or caregiver, such as a blood sample in an appropriate container. Also shown in this view is a pair of rotors 403 and 404, each having a cage 405 and 406 surrounding each respective rotor to decrease chance of fouling of the respective rotor. While shown in this view as a circle containing multiple rectangular bays, drone 401 may take varying shapes, and bays may be disposed at different positions on the drone. For example, the drone may take a generally block shape with bays provided on facing sides, or an irregular shape with bays provided at various positions. Bays may take any shape, including circular or irregular in shape, and multiple rotors would typically be provided. While two are presented in FIG. 4, it is understood that four or more rotors may be employed.

Figure 5:
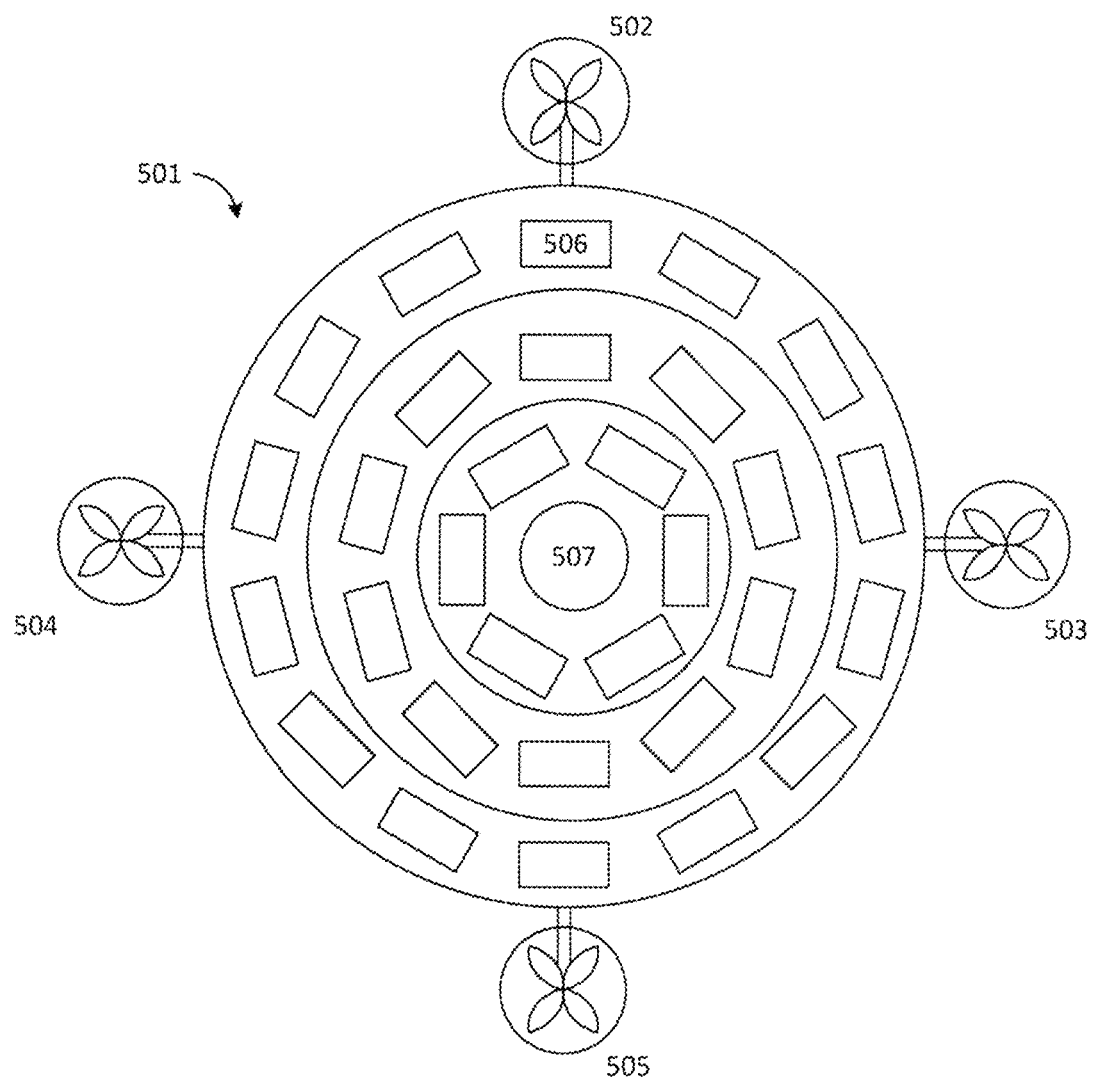
FIG. 5 illustrates a top view of an alternate embodiment according to the present design.

FIG. 5 illustrates a top view of an alternate embodiment according to the present design. In this embodiment, four rotors 502-505 are provided, each having surrounding cages, with drone 501 comprising a number of bays including bay 506. In this orientation, the multiple bays are rectangular in shape and fan outward from a center 507. Again, the doors to the bays are locked and inaccessible unless unlocked, and may include digital screens or other indicator(s) to indicate the intended recipient or transmitter. Certain of the bays may be used for receipt of materials, others for transmission of materials.

Further, in one arrangement, multiple drones may be deployed together, such as on a driver operated or driverless vehicle and/or craft, such that locating each drone to a desired place can take place. For example, drones may be housed at point A, several drones collectively provided to a vehicle near point A, wherein the vehicle transports the drones to point B, and each drone is sent to a desired point or set of points C1 through C27. Such an arrangement may be beneficial when a vehicle is available and flying each drone to and back from a location is beyond the range of the drone, or excessive power is consumed, or certain issues between point A and B exist, such as dangerous winds, vandals, and so forth. Such a deployment may take one vehicle and a driving crew, perhaps as few as one driver or pilot, and less fuel and power than the vehicle traveling to points C1 through C27.

Each drone is rechargeable as disclosed below. When housed on a vehicle, charging or recharging may be provided, and in certain instances, the drone may return to the vehicle, recharge, and travel to a further location.

Figure 6:
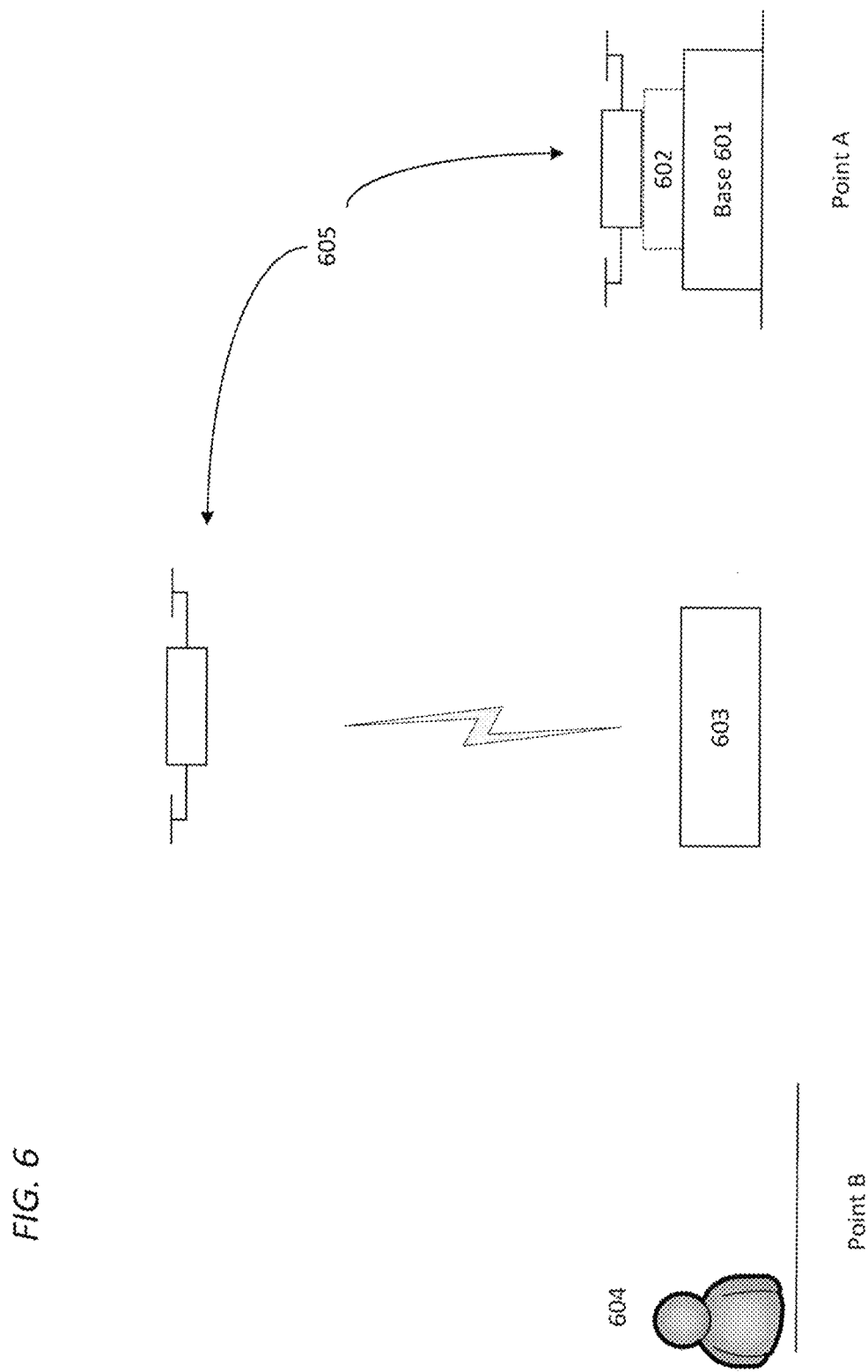
FIG. 6 shows an arrangement of command and control of at least one, and in some instances many, drone devices.

FIG. 6 shows a hypothetical arrangement of command and control of at least one, and in some instances many, drone devices. From FIG. 6, base 601 may include a charging station 602 and may maintain a drone 605 until needed. Control electronics 603 may be manual or automatic and may command the drone to travel from location A to location B. Control electronics 603 transmit over a known frequency and commands are received by the drone 605, and commands may be encrypted and decrypted by the drone 605. At location B, the drone may land or be received, and a charging station may be provided at point B but is not required. Typically point B may be a remote location having no direct connection to the particular drone deployed, such as a residence or facility, and no charging station may be available. The user 604 at point B may receive or encounter the drone and may interact with the drone to unlock a prescribed bay, including unlocking it himself or herself using a physical key, a password received, or may communicate with the control electronics 603 or other remote control device (not shown) to indicate he or she is proximate the drone and wishes to have the bay unlocked. The remote control device may either release the door on the desired bay by transmitting a signal over the air, or may provide the user 604 with an unlock code, or may provide the user with capability to unlock the bay electronically, such as via a local signal such as a Bluetooth signal. Control electronics may be remote but alternately may be provided with drone 605, thus enabling bay unlocking locally.

Once unlocked, the user may retrieve or provide the requisite items to or from the drone, and the user would preferably close the door or a release or otherwise cause the door of the bay to secure the enclosure. As may be appreciated, a bay may be used to provide a medication or other item to a user and then the same bay may be employed by the same user or transported to another user and may receive an item. Once secured, drone 605 may return to point A and may be recharged by employing charging station 602. In another aspect, drone 605 may be deployed to a further point and/or user and may receive or transmit different elements from or two the further user. In all instances, drone 605 ultimately returns either to point A or may return to another collection or securing point, may be recharged, and may be deployed again once all items are retrieved and new items inserted into appropriate bays.

Base 601 and optional charging station 602 may be located on a movable vehicle, for example, or may be otherwise moved or relocated as desired. Control provided from control electronics 603 may be entire flight commands provided initially or may be flight commands provided as the drone 605 progresses through the route, and commands may be provided in real time. For example, GPS information may be collected or assessed by drone 605, with appropriate GPS electronics provided, and flight data such as roll, pitch, and yaw angles may be monitored using for example gyroscopic technologies, and such information may be provided periodically, or at a desired or appropriate or selected time, to control electronics 603. In this manner, if the drone 605 hits difficult winds or for some reason goes off course, commands may be issued to correct the flight path. Alternately, the drone may be equipped to assess its current position and may have map data and may be configured to navigate to the desired point, whether in GPS coordinates, X-Y coordinates, latitude and longitude, etc. A drone 605 at location X may determine no obstacles over 10 feet high exist between its current position and the target location and may fly or be guided to the target in a direct path. However, if telephone lines are present along the path, for example, drone 605 may guide over an alternate flight path to acquire the target location. Such navigational capability provides additional complexity and needed functionality on the drone, but does not require a long range antenna and may require only an initial disclosure of the target location and may navigate to the target without need for further communication.

Figure 7:
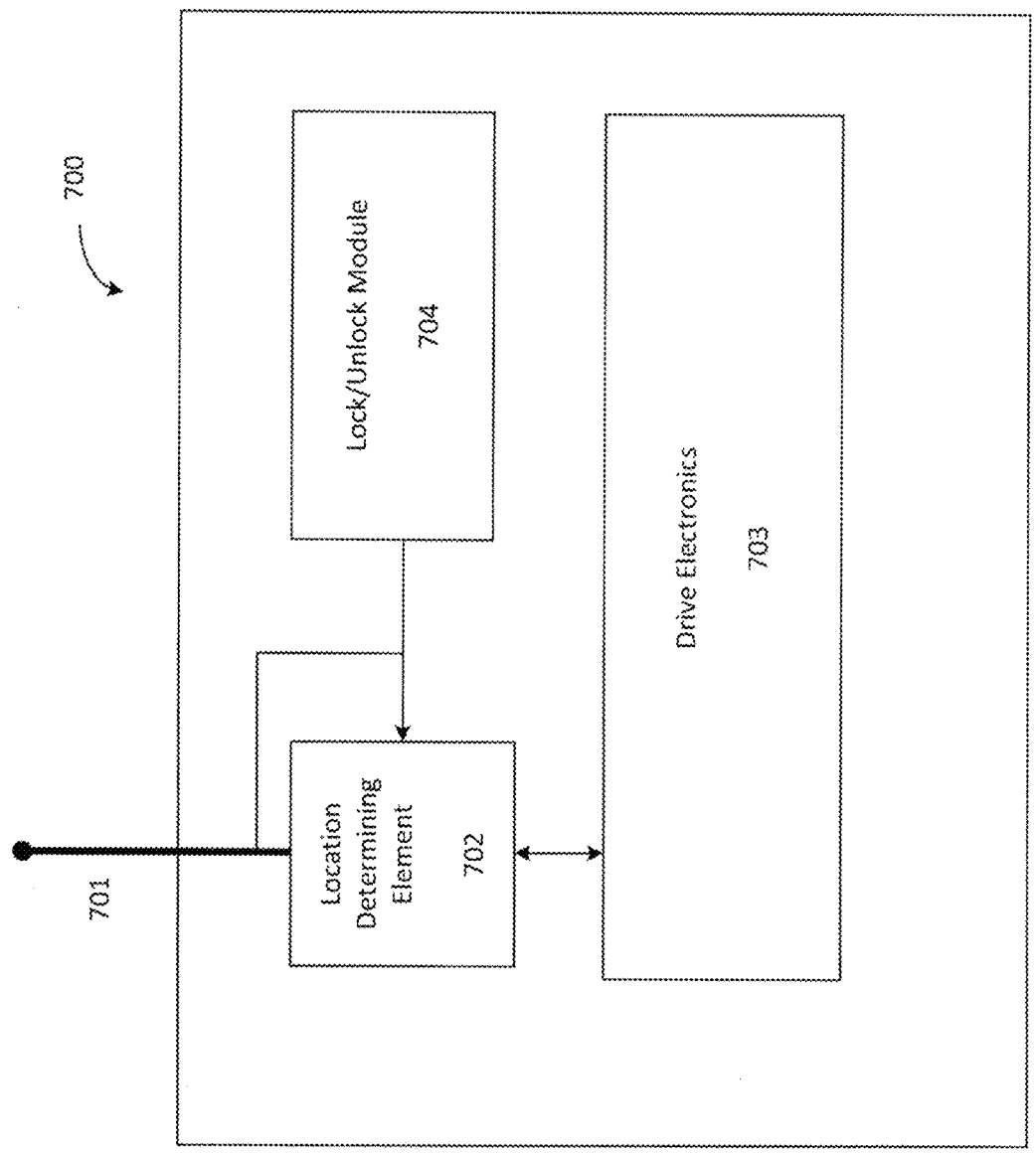
FIG. 7 is a general representation of drone electronics.

FIG. 7 illustrates a general representation of the drone electronics 700. Antenna 701 allows communication between the drone and control electronics 603 when the control electronics are located remotely from the drone. Location determining element 702 may include GPS location electronics, map data, or other functionality to determine the current location of the drone and/or orientation of the drone, as well as the desired flight path based on target location received. Location determining element is optional, particularly if the drone is manually controlled, and may interface with antenna 701 to transmit current flight state variables to the control electronics, such as speed, roll, pitch, and yaw angles, as well as necessary other parameters, such as battery charge level. The information from location determining element 702 may be used to drive the drone and control its path using drive electronics 703, which drive the rotors and control surfaces of the vehicle. Lock/unlock module 704 may interface with antenna 701 to receive a lock or unlock command and may effectuate locking or unlocking of each individual bay provided on the drone. For example, control electronics 603 may transmit an unlock command for bay 2, which may be received by antenna 701 and provided to lock/unlock module 704, which may unlock the door for bay 2, allowing access to bay 2. A corresponding lock command may be received, or the user may simply close the bay door.

Recharging in this arrangement may be accomplished using various hardware. In one embodiment, the drone may simply be connected to charging electronics, such as hanging from a high location, and the drone may dock with or be manually joined to the charging electronics.

Sensors

Figure 8:
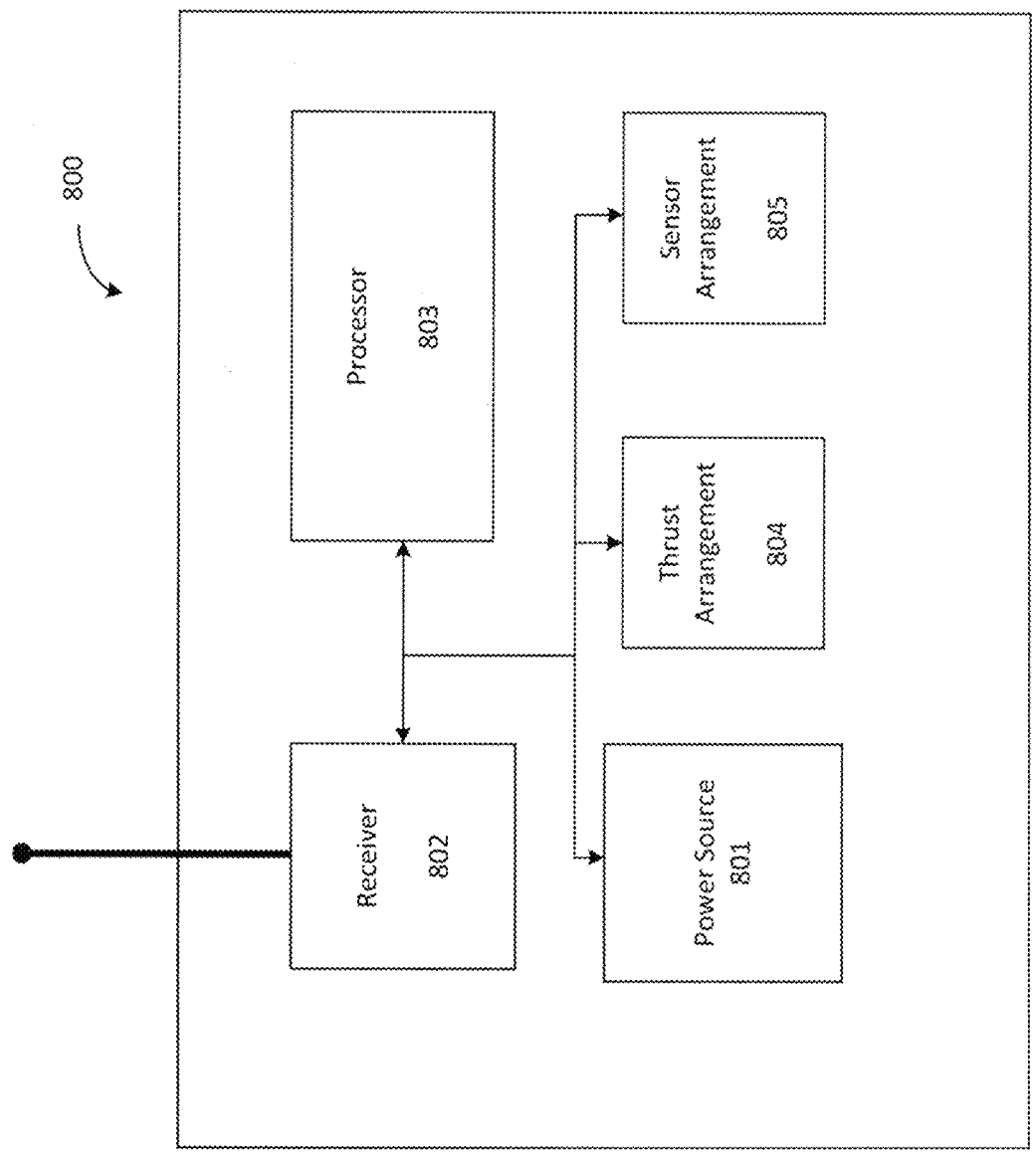
FIG. 8 includes a further conceptual representation of a drone or micro drone according to the present design.

FIG. 8 includes a further conceptual representation of a drone or micro drone according to the present design. From FIG. 8, drone 800 may include a power source 801, a receiver 802, a processor 803, a thrust arrangement 804 including at least one thrust mechanism, and a sensor arrangement 805, which may include one or more sensors. In one aspect, the sensor may be a camera or video device that may be lightweight enough to be supported by the thrust arrangement 804 of drone 800 and may include a transmitter or a storage device configured to transmit or store video data, respectively. In one arrangement, the sensor arrangement comprising a camera or video recording device may interface with processor 803 or an alternate processor to determine the presence of a desired item, such as a person, a reference point, or other visual cue. Other forms of sensor may be provided, including an audio sensor, or a simple senor that senses light or temperature or some other physical attribute and/or phenomenon. Multiple sensors may be provided with the drone, including but not limited to a video sensor and an audio sensor, or in some situations two or more cameras or video sensors with one drone. In some arrangements one or more sensors may be provided with a drone while no sensors or fewer sensors are provided with an accompanying drone. Any combination of sensors and drones may be provided, and certain drones or micro drones may include no sensors or sensor arrangement.

In the case where the sensor arrangement of at least one drone comprises a camera or video sensing device, the drone may be provided with a transmitter that transmits the video information to control electronics 603, for example, or another device where the images may be viewed by a user or other person. Transmission in either direction, from controller to drone or drone to controller, may be by any practical means, including but not limited to RF (radio frequency), Bluetooth, WiFi, microwave, cellular, or other appropriate communication medium.

The drone may be constructed of a lightweight material in its frame or exterior, such as of an aerogel graphene material or other lightweight material. The drone may employ a solar cell for recharging purposes to increase hovering or lift time, and the solar cell may feed a small battery, with both the solar cell and the battery of a lightweight construction. The drone may employ a lithium rechargeable battery or batteries. Any type of thrust mechanism may be employed that is practical, including propellers or miniature jet type engines, for example. The apparatus may be fitted with a digital or mechanical gyroscope, altimeter, and/or accelerometer to determine pitch, roll, yaw, elevation, and motion (speed, acceleration, etc.).

Figure 9A:
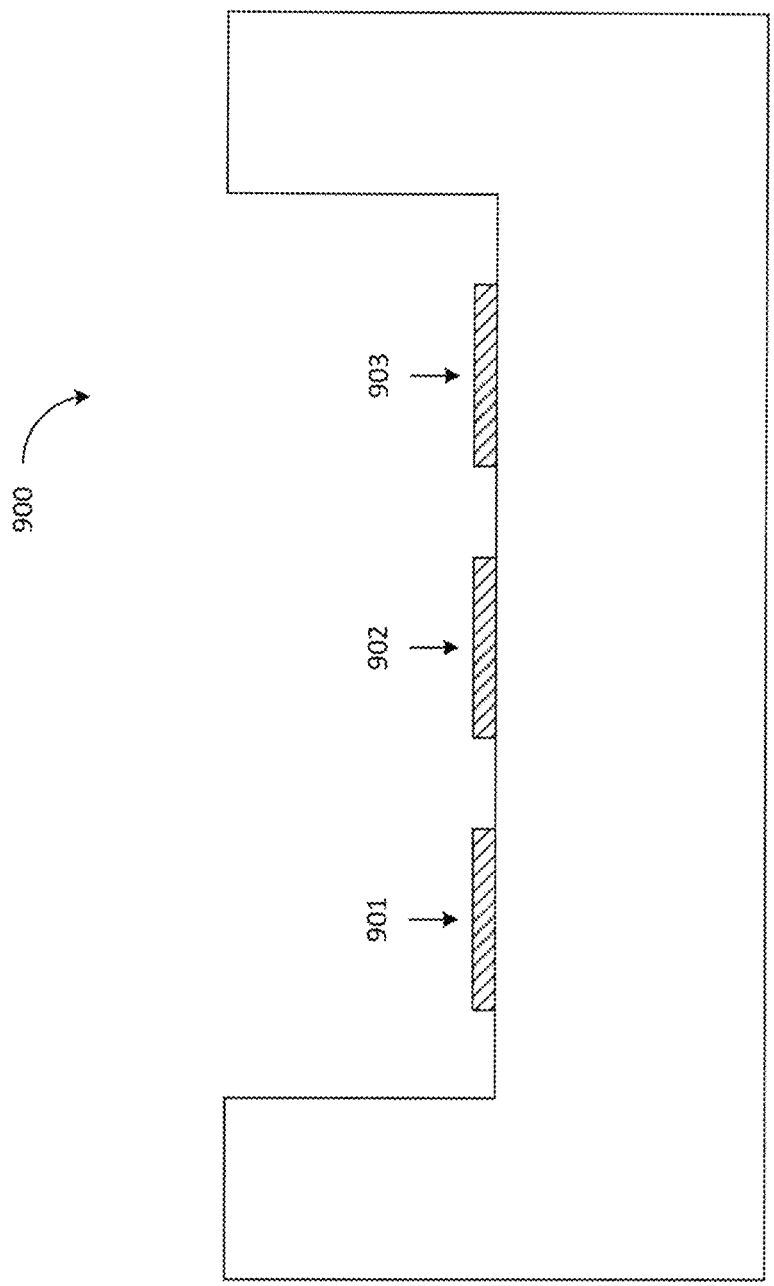
FIG. 9A is a side view of a sample charging station configured to receive and recharge rechargeable batteries.
Figure 9B:
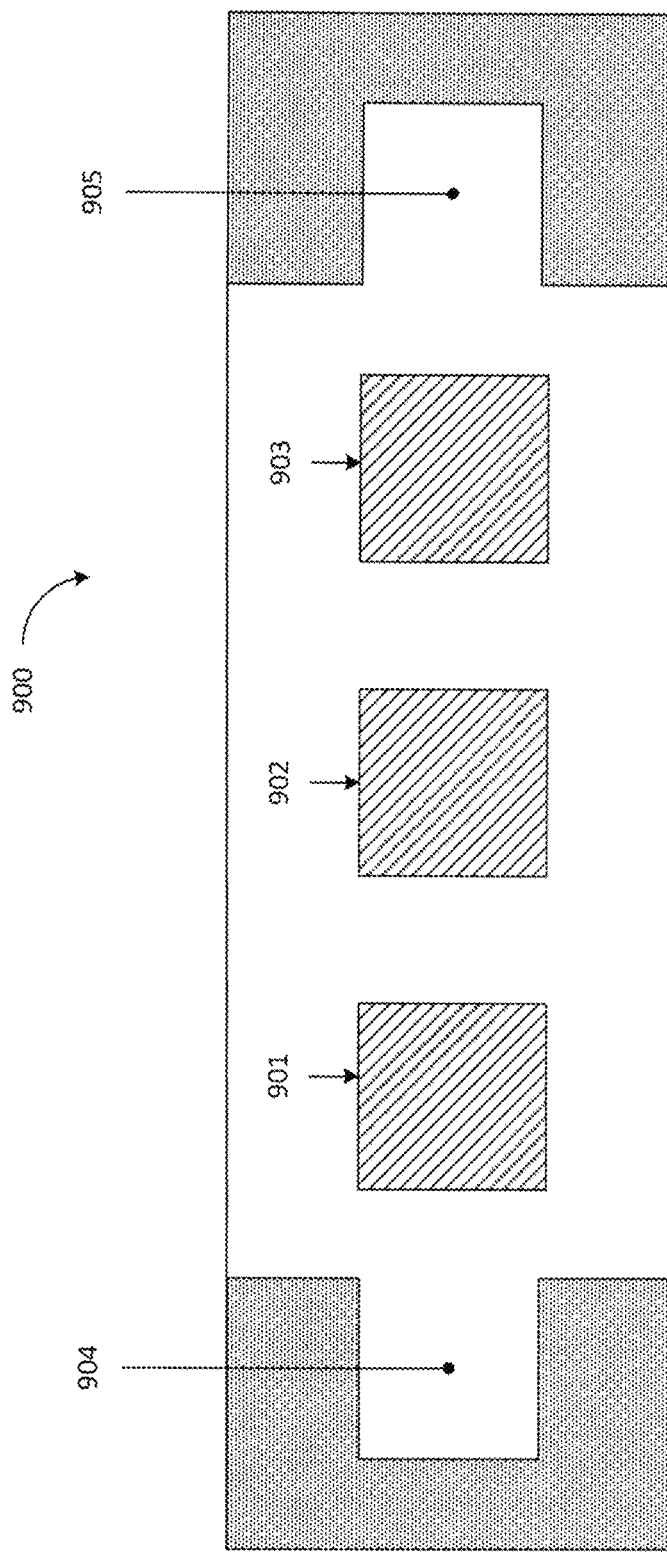
FIG. 9B is a top view of one example of a charging station design.

The present design as noted may include sensors, including a camera or cameras, an audio sensor or sensors, and/or other sensing devices. When the drone arrangement is moving, it may be visually sensing its surroundings, including sensing reference materials, such as reflective bands or reflective item, for example an aluminum impregnated marker. Once these markers have been sensed, the device may transition to a next position, or alternately, the device may sense certain movement, such as movement of a person having a reflective item on his or her body, and may be employed to sense speed of running or even parameters such as difference between desired movement and actual movement, e.g. the user is employing his arms too much while running Charging Station FIG. 9A is a side view of a sample charging station 900 that is configured to receive and recharge rechargeable batteries. Pads 901, 902, and 903 receive the rechargeable batteries, where the receiving batteries are placed in contact with or proximate pads 901, 902, and 903, or at least one of the pads. FIG. 9B is a top view of the charging station design, with pads 901, 902, and 903 shown and openings 904 and 905 presented to receive drone hardware.

Figure 10:
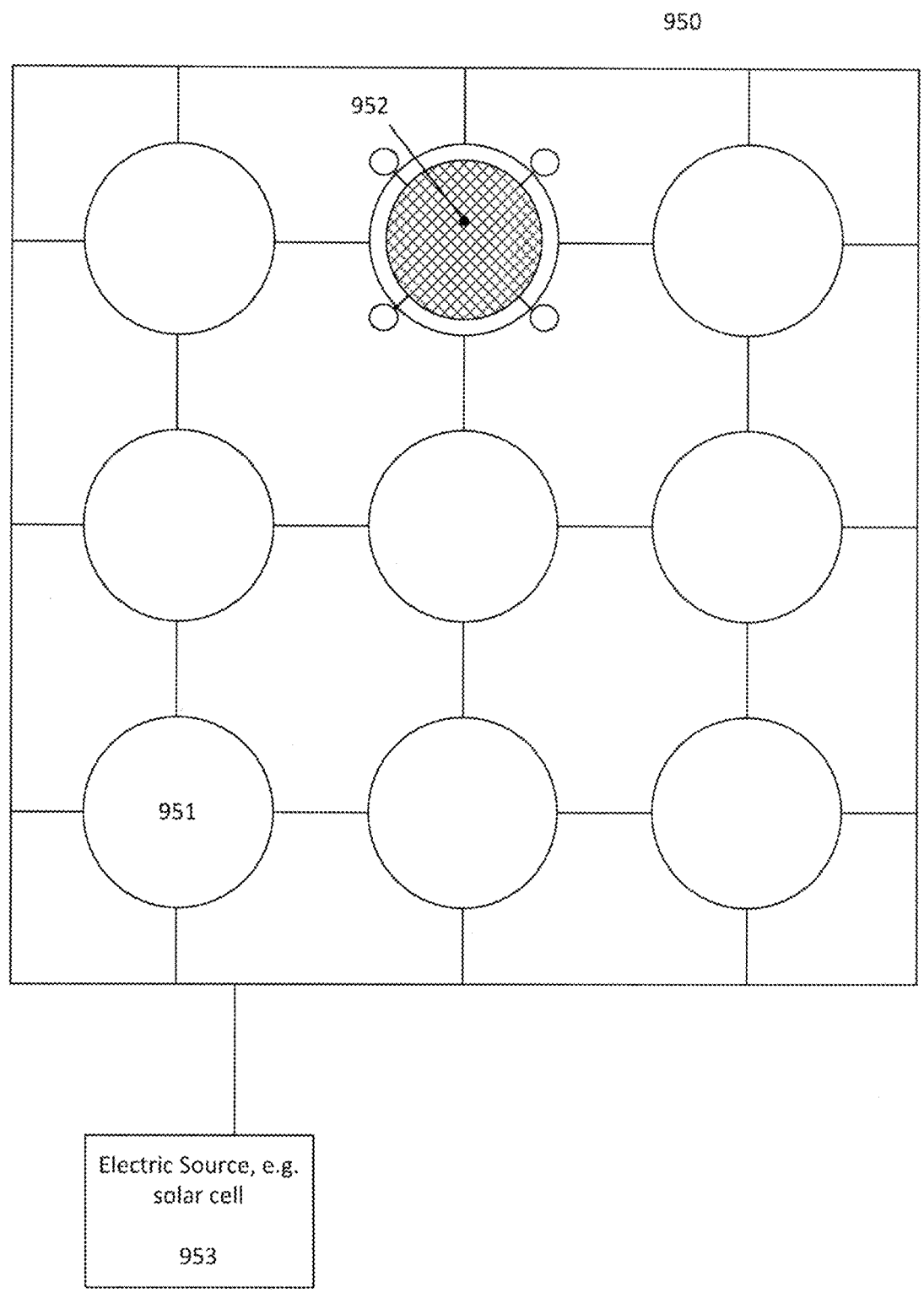
FIG. 10 illustrates an alternate multiple unit charging station.

FIG. 10 illustrates an alternate multiple unit charging station 950, with an empty charging station 951 shown as one of nine in this embodiment. Drone 952 is charging at one station, and this arrangement can accommodate nine such devices. The charging station 950 is powered by electric source 953, which may be a solar cell, wall outlet, battery, or other appropriate power source.

As may be appreciated, rechargeable batteries are known, and recharging of such batteries may be accomplished by an exposed surface meeting with another exposed surface, and lithium ions travel from the charging station to the battery cell being charged, and in the case of lithium-ion batteries, from a positive electrode to a negative electrode through an electrolyte. Such rechargeable lithium ion batteries should be lightweight and allow for a relatively lengthy period of drone/micro drone operating time.

While not shown in the present drawings, the present design may include solar cells as primary or supplementary power sources. Such solar cells may be provided with the drone or with elements attached to the drone that powers the drone.

Contactless Patient Assessment

The present design may include hardware configured to noninvasively assess health attributes of a specific user or patient. The present design may take the form of a device including a drone and at least one sensor and in certain instances more than one sensor, such as a camera and an audio collection device, where the device has processing and communication capability. In this manner, an individual can be located proximate a drone device at any desired location, such as her residence or place of work or elsewhere, that can be configured to meet her personal care needs, including medical needs, and can provide noninvasive assessments of patients using the hardware provided. In one embodiment, the user/patient may also enter information manually and the information may be received at the drone.

In one embodiment, information received may include bowel sounds and sounds emanating from joints and other body parts. Such sounds may be assessed and recommendations or suggestions presented. In such an embodiment, the apparatus comprises a sensor configured to receive spectral gas data including body organs spectral gas data emanating from the mouth, bowel or sweat glands of a patient.

The system may include a portable device configured to be taken with the user/patient, while traveling locally or long distance, and the portable device may connect with the base device such that the user may record desired information and provide the information to a central location, such as control electronics 603 or a network operations center, at a later time.

The present system may include a communications network, which may be server or cloud based, wherein the user/patient can store personal care information, obtain personal care information such as recommendations specific to the user, and may schedule and receive reminders, and so forth.

Communication may be effectuated between a base station, or processing and storage site, and one or more drones in any manner known and available, including but not limited to internet connectivity via wire, wireless (802.11a/b/n/g, Wi fi), cellular, and or other communication means. More than one such site may be employed and more than one such site may carry out some of the functionality disclosed herein.

In operation, user interaction with the device and/or modules may entail the collection of data that may be retained at the device, with data provided from modules to the device via WiFi, Bluetooth, or through a USB connection or by any other means known in the art. The processor at the device may process the data using device formulas and/or applications and may format the data into graphs, charts, diagrams, virtual assistants and other forms to be displayed to the user via, for example, the device (2D, 3D, or holographic) screen. The data and/or information may be controlled by the user and may be sent from the device to a remote location, i.e. a virtual "cloud," where the information may be collected, analyzed, and/or stored. Once transmitted to the remote devices, the user information may be maintained, analyzed, and specific user recommendations or information may be transmitted back to the user. As currently configured, varying levels of service may be provided. As one example, a gold/silver/bronze level of service may be provided, wherein bronze is simply maintaining data at a remote site, silver is analyzing data and providing recommendations, and gold is a concierge type service where the user may be provided contact with available personnel (physicians, pharmacists, personal shoppers, cosmetics specialists, optometrists, dentists, etc.) and particular needs will be addressed. Different or alternate levels of service may be provided.

As may be appreciated, virtually any type of information may be collected and/or provided using the device/module arrangement provided herein. The ability for the user to indicate specific needs and desires via a keyboard and possibly a mouse, and for the device to display information and act as a mirror enables a virtually unlimited range of functions. A particular user may wish to receive clothing recommendations and may have her skin tone and hair color determined, and clothing color recommendations provided. Body type may be determined, and age entered, and age appropriate wardrobe selections may be provided based on an analysis provided from the remote location. Another user may have a blood sugar issue, and his blood sugar may be monitored and tracked, and based on his history and desires, recommendations as to what to eat and/or when to eat may be provided to the device and/or to the handheld unit. Another user may want to monitor stock quotes and baseball scores in addition to tracking his progress on a weight loss program. While providing stock quotes and baseball scores is not strictly a personal care function, the present design may offer any type of functionality offered by a computing device and/or tablet and/or smartphone. The user may be exercising with the handheld unit tracking his progress, i.e. time spent exercising on a treadmill, while the device may display stock quotes or baseball scores. At the end of the user's workout, he may weigh himself using the scale module and may receive meal recommendations and/or a graph of his exercise progress or weight via the device. Thus single or multiple functions and determinations may be provided or made based on functions, applications, and computations available, as well as the needs and desires of the user, in addition to the functionality provided at the remote device arrangement.

Organ Health Assessment

The present design is applicable in the telehealth field, where telehealth contemplates the remote evaluation and management of the health of individuals. The present design enables a healthcare provider to perform a contactless noninvasive physical assessment of a patient or patients using artificial intelligence or other functionality to perform evaluations of various bodily organs and/or body components. Such assessments can provide evaluations yielding reasonable results equivalent to the generally accepted current methods of physical examination (inspection, auscultation, palpation and percussion) but from a remote location.

The present design employs a drone that may use at least one camera, microphone and/or sensor to obtain specific direct measurements including but not limited to intensity of skin coloration, temperature, hair follicle displacement, quivering, fasciculations, constructed and deconstructed multidimensional, directional and non-directional sound waves, spectral gas analysis of emanated body gases, as well as other noninvasive single or multiple data points measurements related to the inferred, predicted and validated body organ vital sign.

The drone may provide the collected information to a remote system, such as a collection and assessment system, that allows user interaction and data collection to track the health of the user, for example. One such system is described in U.S. patent application Ser. No. 16/027,352, entitled "System for Remote Noninvasive Contactless Assessment and Prediction of Body Organ Health," inventor Ayman Salem, the entirety of which is incorporated herein by reference. The present system in its entirety, including the drone arrangement described and the remote system, may provide a method of generating a prediction model for body organ health. The system determines vital signs of interest by providing more than one data point source entry with a Model Deconstruction Transfer (MDT) platform comprised of a variable library (VL), wherein each data point enters at least one data set relevant to the vital sign of interest into the MDT platform and selects variables from the VL that are relevant to the vital sign of interest. As an example, when assessing heart health, skin color may be assessed and used as a data point. Such a data point may range in importance anywhere from zero to 100%; the system accounts for the information provided, particularly in conjunction with other information collected, and makes its best attempt to assign weight to the different observations, which may occur over time, and assess health of the patient, particularly his or her organs. Further, the present system may generate at least one prediction model (PMo) for each vital sign from the MDT platform, wherein each PMo is based upon the selected variables. Heart rate, observed pulse, skin color, blood pressure, and so forth may all constitute data points.

The system may also generate a Model Component Library (MCL) from each PMo, wherein the MCL comprises components that result from deconstruction of each PMo. For example, on a Tuesday the system may sense the patient has a skin color, heartbeat, blood pressure, general disposition, and weight. Such readings sensed may be deconstructed and stored in the MCL and subsequent readings may be collected such that the system may at a later point assess patient health, such as organ health. The system may generate at least one second prediction model (PMI) from the MCL, wherein the system employs the at least one PMI to predict the probability of the health vital sign of interest to the healthcare provider for a specific user. As many be appreciated, the system may determine that a user with a current heartbeat of X, blood pressure of Y, smoking history of Z, heartbeats of A1 through A60, representing 60 readings of heartbeat, a blood composition of B, skin color of C, and current body temperature of D may have a risk of stroke of EE, risk of heart attack of FF, and risk of lung cancer of GG. In the system, logic trees and/or other artificial intelligence techniques may be employed. The system may generate a PMI using individual MCL components as variables in the at least one PMI with differential weightings. A single MCL component may be used more than once in a single PMI. For example, a skin color of C may be used in assessing the health of multiple organs or systems in the patient. Further, each use or a single MCL component may be subject to a different statistical limitation. In one instance, skin color may have high importance in assessing and may be assigned a value of, for example, 50%, while in another assessment skin color may have an assessment value of 1%.

The present system further provides a method of generating a prediction model of a vital sign of interest. The system is configured to obtain at least one data set relevant to a vital sign of interest, select variables from each data set relevant to the vital sign of interest, generate at least one first prediction model (PMo) of each vital sign based on differential weighting or at least one data set variable. The system generates at least one PMI and may further generate a Model Component Library (MCL) from each PMI. The MCL comprises components that result from deconstruction of each PMI, and the system may also generate at least one second PMI from the MCL based on a differential weighting, or the MCL components relevant to the vital sign or interest. In one embodiment, the one or more body organ vital signs may be provided by the system to a Model Deconstruction Transfer (MDT) platform comprising a variable library (VL).

In operation, the system may make a number of assessments of a patient, in one sitting or at various times. The assessments are done using contactless physical "capture points" from a single device, or from data stored and exported from other similar devices with historical data entry points. Such capture points may include different readings captured at different points on the patient's body, either during a current test or stored data from previous testing. A patient may have her body temperature, blood pressure, and pulse taken over a period of time, and may have available various blood, urine, and stool samples available by visiting a location wherein the information pertaining to the samples is provided to or received by the system. Further, the system may have available information about the patient, such as age, gender, blood type, known allergies, previous medical procedures performed, and so forth. Information available about the patient collected by the system in these various manners may then be deconstructed to determine relevant attributes and create a prediction model based on this information. For example, if the user has a pulse of 81, the system may build a model for issues when the patient's pulse reaches 90, 100, 70, 60, or other specific values, including risk of stroke, unconsciousness, and so forth. Models may employ multiple patient attributes, primarily know attributes but also including unknown or assumed attributes and attempts to build at least one model predicting a possible course for this patient. A further example may be that information about a patient's heart may be available and based on the information the system may determine that if the patient continues on with his or her current course, he may run an X % risk of having a heart attack or a Y % risk of stroke within the next five years. Such assessments are based on evidence based medical science including statistics and other available relevant information.

Other information may be available, such as information provided by the user, for example representations of his diet or physical activity, mood, stress level, and so forth. The system may have multiple pieces of information relevant to the user available and may employ all information or only certain information in creating prediction models. The MCL may include components from one or more prediction models, such as an expected blood pressure at a point in the future assuming all other actions remain consistent, and such MCL components may be current or forward looking, such as at some point in the future (future white blood cell count, future oxygen intake capacity, etc.) Hence one parameter, such as red blood cell count, may be isolated and used in different models and libraries and may be available for use in prediction or use in a prediction model.

The system may alternately or additionally obtain a further data set from one or more body organ vital signs, wherein this additional data set comprises other body organ vital sign data not represented in the MCL and is thus non-redundant and unrelated to data used to generate the MCL.

This additional data set may include a training set, used for training the system and including either hypothetical or actual attributes, a test set using test information, wherein test information may be used to evaluate hypotheses or models created and typically include previously determined or available data. Alternately, additional data may be provided as a combination of a test set and a training set. Data in a data set may be divided into training and test sets chronologically according to the time of recording.

At least one PMI may include MCL components selected based on performance of the PMI to predict probabilities of the body organ vital sign in the training set or the test set. In such a configuration, when predicting for example heart health and blood pressure, prior blood pressures may be employed in the prediction model, and MCL components may include such prior blood pressures.

The system may generate at least one PMI from the MCL using individual MCL components as variables. In this scenario, the system may use at least one PMI with differential weighting. The system may use a single MCL component more than once in a single PMI. Each use of a single MCL component may be subject to a different statistical function. For example, in one instance criticality of white blood cell count may be zero, in another 20 weighting, in another 50 weighting, and in another 81.3 weighting. Value of the attribute may be a function of other attributes.

A few specific examples are provided. In certain instances, the following examples may be used in the system to validate and predict body organ related vital signs. In the case of heart health, including but not limited to heart rate, blood pressure, cardiac output, vascular resistance, pulmonary circulation pressure, and so forth, the system may take multiple measurements from predetermined body locales, peripheral or axial, either by a healthcare provider or using a 2D or 3D or holographic representation of the user's body, by touching the user's displayed 2D, 3D or holographic image or by the user touching an appropriate part of his or her body with his or her finger. Alternately, the system may determine such parameters using a preliminary scanning data sourcing algorithm that determines a preferred noninvasive data point sourcing from a desired physical point. The physical data sourcing point location is fixed and stored in the system using body surface navigation techniques and retrieved for future reference for data point sourcing.

Regarding representations of the body, such as 2D, 3D or holographic representations, certain technology may be available wherein information about the user's system may be gathered, such as heart attributes, stomach attributes, intestinal attributes, pancreas attributes, circulatory attributes (blood vessels, etc.), bone attributes, brain attributes, and so forth, either by scanning, examination, assumption, or otherwise, and such information is represented in a 2D, 3D or holographic model of the patient, and information may be gathered from this 2D, 3D or holographic model. For example, a patient having undergone heart bypass surgery may have veins removed from his person and inserted in proximity to his heart, and the 2D or 3D model or holographic image may reflect the absence of veins and/or the presence of veins and stitches, etc. near his heart. A patient known to have a brain tumor may have her brain radiographically, anatomically or otherwise represented with the tumor therein such that a remote physician or the system may account for the size, shape, and quality of the tumor. Other representations, such as unknown attributes of the user, may be generic in quality or quantity. For example, a woman with a brain tumor may have no information available about her femur, and a general or generic representation of her femur may be provided for a woman of her size. Information known about the patient may be used in representing unknown organs or body parts. The result is a general model of a patient's body which can be used to assess his or her health in various circumstances and can be modeled to operate in an expected manner based on prior information—for example, heartbeat can be modeled based on known attributes of the heart and prior measurements, such as blood pressure, pulse rate, cardiovascular health, and so forth.

With respect to heart health, in one example, the system uses multiple points of reference, wherein the user may touch one point peripherally on his forearm, one point axially on his face, and one auditory data point related to the organ in question, such as the heart. Data point inputs from a camera, microphone and a sensor located on a drone in accordance with the depiction provided herein may be retrieved or obtained where relevant and information gathered is constructed to a single data model. For example, the system may transform sound energy from the microphone to a visual geo-localized three-dimensional image from the "Lub" (systolic) and "Dub" (diastolic) sound wave of the heart. Pixel to pixel convoluted neural network (CNN) analysis of the image may be employed, for example, to render predictive correlations with other heart related parameters not limited to systolic and diastolic blood pressure, stroke volume and cardiac output. Convoluted, recurrent or any other type of software or hardware artificial neural network inspired by biological neural networks may be employed in this process. Reconstructed auditory images of the heartbeat can include additional information regarding axis of heart rotation, velocity of blood column, valvular auditory inputs, blood viscosity, electrical signal spread in the bundle of his or other heartbeat signal attributes. Additional readings from distant areas may also augment heartbeat information, with the visible pulsing of veins and arteries under the skin of the user. Although data is received as different forms of energy, such as sound energy versus light or visual energy or other readings, the system transforms differently sourced data points (one or more) to one uniformly comparable data format. The system compares and correlates the different data sources to a referenced vital sign, such as pulse or blood pressure. The measurements taken by the system can be recorded and used to train the user specific model of the individual patient to verify or validate a predicted blood pressure. The system may also test the user specific AI model to fine tune prediction accuracy. The system may employ attributes of a patient, including attributes retrieved, calculated, and/or predicted, with other patients by matching attributes between patients, including but not limited to genetic and physical attributes of individuals. The system compares a predicted vital sign value with the actual measured vital sign and may correct for the difference by re-adjusting the different weights previously rendered, continually fine tuning error margins and narrowing the gap between actual and predicted values.

For example, if patient X has a certain BRCA genetic makeup and developed breast cancer at age Q, and patient Y has a similar physical makeup and BRCA gene distribution or profile, Patient Y may be expected, with a level of uncertainty, that she may contract breast cancer at a similar age. In this manner, the system may obtain, calculate, or predict other heart related vital signs that can be evaluated and/or correlated to diagnose and manage heart diseases, for example.

In the case of lung health, including but not limited to respiratory rate (RR), $CO_2$ level, lung volume, pulse oximetry, breathing characteristics, jugular vein distension (JVD), pitting edema, and/or body pH level, the same general overall concept applies. The system may obtain oxygen saturation via pulse oximetry ($SaO_2$) by the user directly putting his or her finger on a body location collected using a camera in addition to noninvasively obtain the lung sounds at apices or bases of the lungs. The system collects or correlates such measurements with chest wall expansion using two observation points on the exterior of the patient or chest wall spatial excursion. The system, from this information, may determine a value, known as the FEV1/FVC ratio or Tiffeneau-Pinelli index used in the diagnosis and management of restrictive and obstructive lung diseases. The system may obtain other lung related vital signs and may correlate collected information for the diagnosis and management of lung diseases. For example, as described herein, the system may use a microphone, camera, and other components, including but not limited to other medical sensing mechanisms to sense attributes of the patient, either visually available, audibly available, or otherwise available to make the determinations and assessments provided herein.

The system may also determine vascular health. Vascular Health in this sense may include, but is not limited to, vessel pliability, temperatures of hands or feet, hair loss, ulceration, atrophy, and/or skin discoloration. The system, including the drone discussed, may employ a camera to measure the degree of two or multi points displacement of, for example, hair follicles due to superficial pulsations of a midsize artery like the radial artery at the wrist, or the patient's superficial temporal artery in the temple area, or a large size artery such as the carotid artery in the neck. The system may correlate these visual data points with visually transformed images of heart sounds, and in this manner the system can establish a vascular wall elasticity index. Such an index may facilitate the diagnosis and management of vascular disease.

The system may also assess, predict, and diagnose issues with skeletal health, including but not limited to deformities, warmth, swelling, range of motion (ROM), and/or presence of scoliosis. The system, in one embodiment including the drone provided with a microphone or other auditory sensor, noninvasively assesses sounds emanating from joints and correlates such sounds to visual cues from specific joints e.g. range of motion, deformities, warmth, and swelling. As a result, the system establishes a flexibility index used in the diagnosis and management of each body joint health and disease state.

In the area of gastrointestinal microbiota health, the system noninvasively assesses sounds and gases emanating from the patient's gastrointestinal tract and correlates such sounds and gases to an axial and peripheral skin perfusion color analysis as well as heart sound. The system indirectly assesses gastrointestinal perfusion and generates and follows a digestive index that can be used to assess the gut microbiota and their response to different foods or pharmaceuticals, as well as ingestible items that can be avoided, and any change in the gut microbiota that may result or influence the gastrointestinal health or disease states.

The system may auditorily receive and assess bowel sounds, where such sounds represent the intrinsic gastrointestinal secretions as well as gas produced by gut microflora or microbiome. The gas content (echo chamber) of the bowel reflects the metabolic activity of the gut bacteria (microbiome) and such metabolic activity is reflected in the heart rate and blood pressure of the patient via the gastrointestinal-brain connection. The immune system is also involved in this delicate dance with fluctuation of body temperature related to "capillary gating" that allows nutrients as well as chemicals and some bacteria or their byproducts to cross over to the blood stream, causing some antibody immune response. The system, monitoring bowel sounds and other available information, may provide a recommendation such as "adjust your carbohydrate intake by 50 grams per day, to avoid gas distention and increase in your heart rate" or "your temperature was elevated following this protein rich meal and an immunoglobulin blood assay test was ordered to be done with in the next 30 minutes," with blood recommended to be drawn, such as by a health band, and analyzed immediately or at a later time."

The system may also assess sleep architecture health. Healthy adults typically need between 7 and 9 hours of sleep per night to function at their best. Most of the brain reparative processes happen during sleep. Sleep architecture refers to the basic structural organization of normal sleep. Two types of alternating sleep cycles exist, non-rapid eye-movement (NREM) and rapid eye movement (REM). Irregular cycling and/or absent sleep stages are associated with sleep disorders. Cardiovascular, respiratory, sympathetic, renal and endocrine body stems show physiologic changes that occur during sleep. While a user is asleep, if appropriate for the use of a drone employing a microphone or other auditory collection device, the system may assess sounds of turning on bed and degree of snoring or breathing, and these sounds can be correlated with heart rate and other visual cues to noninvasively assess and follow the sleep architecture health.

The present system may seek to statistically "curve fit" and compare predicted data points using known predictive analytic techniques to actual data points. The system also employs contextual adaptation techniques to narrow the gap in curve fitting between multiple, such as three, elements of prior historical statistical analysis, current real time data points and predicted future values of data. The present system uses synthetic control of data points with "go/no go" methodology that allows data points above a certain predetermined weight to enter into the assessment and recommendation process described herein.

The present system thus obtains, assesses, and predicts body organ vital signs noninvasively by combining visual, auditory and other sensory data sensed from a device such as a drone hovering proximate the patient, where the drone or device has a camera, microphone, and access to other relevant medical assessment equipment, potentially joined to the system via a network. The system may also receive patient data from other sources, such as external sources at single or multiple "capture point(s)," and may determine information about organ health from peripheral data or statistics. The system also tracks body organ health and disease states remotely and noninvasively using a device such as the drone arrangement or arrangement of drones described herein together with other system components described. The user may enter information—foods consumed, mood, general health, specific health, via the devices presented herein.

The present design thus provides a drone arrangement that is configured to receive, from a sensor configured to detect blood distribution analysis and spread at two or more regions of a patient or user via patient skin color, tone, temperature, condition (dry/soft/firm/swollen/sunken), and capillary refill. The system may, in this instance, receive an image indicating a first blood distribution and spread for a first region and another image indicating a second blood distribution and spread for a second region. The system may compare the first blood distribution and spread for the first region and the second blood distribution and spread for the second region to provide a blood-distribution/spread asymmetry representing a difference in heart health between the first region and the second region.

Alternately, the system may receive and compare data from a microphone sensor capable of detecting body organ sounds. Data is captured through a microphone sensor targeted specifically and compared to the same physical point location of a body region on the patient. The system compares capillary refill, with different data obtained from different sensors (optical, infra-red, tactile, etc.) as well as a microphone to indirectly or directly infer and determine respiratory rate (RR), lung volume, pulse oximetry, breathing characteristics, jugular vein distension (JVD), and/or body pH level, pulse/heart rate, blood pressure, heart rhythm, and EKG values using appropriate hardware and hardware modules. The device may collect, compare, and measure data either directly or using processing to directly or indirectly infer a body organ measurement from a baseline measurement. As such, the system assesses body organ health, and generates a specific health suggestion to the user in one embodiment.

Alternatively, the system may receive and compare data from a device such as a gas spectral analysis sensor capable of detecting different gases emanating from body orifices or skin. The gut—brain axis is a communication system that integrates neural, hormonal, and immunologic signaling between the gut and the brain and other organs, offering the intestinal microbiota a potential route to access and influence multiple body organs. The gut microbiota is implicated in nutrient acquisition and energy harvest and produces exo-metabolites, such as short chain fatty acids (SCFAs), that may regulate a host metabolic process. Gas chromatography-mass spectrometry or other means can noninvasively assess both mouth odors from halitosis or fecal gases not limited to butyrate. Oral, gastrointestinal and related organs like tongue, salivary glands, liver and spleen can be remotely and ono invasively assessed. The system may assess these factors or characteristics and may provide health suggestions by applying the current methodology.

While the drone in this instance may be hovering in front of the patient, as an alternative, the provided elements, such as the camera, microphone, etc. may simply be positioned in front of the patient by the patient or a third party. Such operation can be beneficial in the case of difficulty obtaining readings while hovering. In such a situation, the drone may fly to or otherwise be transported to a point near the patient, and the drone may be collected by the patient and relevant equipment, such as the camera, microphone, etc. may be manually placed in a desired orientation near the patient. The drone may then be used to collect the data, and the drone may return to a desired point, such as by flying in a manner depicted herein.

The system initially collects information known about the body part, either previously assessed or predicted or calculated. The system assesses further information using the system hardware disclosed herein, including video, audio, and/or other sensing functionality. The system creates at least one prediction model based on data collected and establishes a model component library based on data contained in relevant prediction models. The system may provide vital signs to a Model Deconstruction Platform, which deconstructs the model into component parts, where the Model Deconstruction platform includes a Variable Library representing variables applicable to various patient attribute assessments and predictions. The system may create or enhance a representation of the patient based on relevant information, wherein the representation may be 2D, 3D, holographic, or even textual or any other form of patient representation known in the field. Point 2008 is the system assessing at least one patient attribute based on available information, such as visual determinations from multiple points of the user's body, visual determinations and audio determinations, etc. The system may predict patient attributes or a single attribute and may optionally provide the prediction to the patient. Again, such predictions depend on circumstances but may be as mundane as "if you do not take aspirin, you run the risk of further wrist pain" to "you may be at elevated risk of cancer in less than 8 years."

Individual or collective vital readings, organ assessment and or recommendations employ the blockchain concepts disclosed herein, i.e. are provided on a distributed ledger format, to aid different health providers to review, assess or retrieve information for further clinical management, third party billing, or other administrative related activities. Blockchain provides regular, such as daily, reporting that includes entries of desired categories (e.g. food, beverage, activities, symptoms, medicine and vitals) in addition to recommendations, wherein recommendations are determined either via artificial intelligence or provider interactions, and/or recommendations for a specific date of service.

The system may self train. In one example, if today's measured blood pressure is 140/90 the system accounts for all available information such as calories, symptoms, medications, activity, weather, season, GPS location, genetic factors and other factors, and may predict a number for blood pressure at a specific time the following day. The patient measures his/her blood pressure on that specific time the following day. The system accounts for any difference between actual and predicted measurements and creates a training set of systolic and diastolic numbers to adjust future prediction accuracy. Such test/correct processing continues as long as necessary to lower the probability of a successful reading to as low a value as possible. For other vital signs, such as heart rate, readings can be assessed using available devices such as a health tracker or other peripherals, or contactless in some situations.

The system may call for a blood sample at certain times, wherein blood drawn may be analyzed instantly or later to train the system further. Training can include radiological, laboratory or other diagnostic data. The system obtains patient history, performs a physical exam, and orders tests. The system then diagnoses based on known information to be able to recommend different management options. The system may employ auditory sensing to receive a conversation between doctor and patient, and may assess doctor textual entries to make recommendations.

In general, during operation, the user/patient positions himself/herself in front of the drone device, or the drone device is positioned in front of the patient and/or sensors, or uses the modules available. The user points to area of symptomatology. Sensors focus on this area, determined by sensing the user finger and the region proximate the tip of the finger, and gathers visual data noninvasively. Sensors may gather data from other areas of the body. The system may determine or call for other relevant sensor modalities to gather further information from the area in question or other related areas. The data gathered may be represented textually, or in a 2D, 3D, or holographic representation of the individual (heart size, bone attributes, brain attributes, etc.), and/or may be represented on a holographic avatar. At this point, the system may initiate processing, by consulting with known information and/or recommendations, and may determine and present diagnostic recommendations. Such recommendations may be provided to the patient, insurance representative, or other authorized individual or entity, and desired milestones may be provided or assessed. The system may then create, for example, a blockchain record, and may employ a blockchain methodology similar or identical to that shown in U.S. patent application Ser. No. 15/943,585, filed Apr. 2, 2018, inventor Ayman Salem, entitled "Enhanced Personal Care System Employing Blockchain Functionality," the entirety of which is incorporated herein by reference. Further attributes of the blockchain functionality employed, specifically the anonymization aspect, are discussed below. Further, the user/patient may be incentivized at each agreed upon milestone with health cryptocurrency or other incentives, with such information provided to the blockchain.

In the specific case of obesity and depression, the user/patient positions himself or herself in front of the device and/or sensors. The sensors gather auditory data from gastrointestinal tract, as well as heart rate, skin perfusion, user voice and an emotional analysis, which may be administered by a series of questions or may be based on factors such as posture, expression, and so forth. The system predicts future weight and a future depression score, and these may be provided to the patient. The system may offer communication capability for the user to communicate regarding his or her predictions with the system or a professional. The system may then, based on knowledge of the medical fields of obesity, diet, nutrition, etc., develop a set of diagnostic recommendations. Milestones can be planned, discussed, and/or approved by a provider or insurer, as well as with the patient/user and other third party. The system may provide to the user an incentive methodology incentivizing change in patient behavior, and such may be approved by an insurer or other third party, or by the provider, and the patient/user. The system may create and distribute a blockchain record.

One additional attribute of the present design is that during a provider—user interactive session (or sessions), data sources from different audio, visual or other data input(s) can be transformed into a unified data source and be processed as such. For example, the conversation between a provider and a user can be transcribed to visual text and the system can weigh symptoms shared by a user based on speech and facial expression sentiment analysis. Spoken words by both user and provider in this example are transformed to one or multiple 2D, 3D, or holographic visual representations to be entered in "go/no go" data processing for the specified body organ. The system can search and retrieve the unified data source in the transformed or original format(s) as to facilitate bodily organ health assessment(s).

Additionally, in the specific area of neurological and mental health, speech analysis is not necessarily limited to sentiment, anxiety, irritability, contentment, aggressiveness or other speech dysfunctionalities and may include dysarthria, dysphasia, staccato, and/or scanning type of speech. The system can analyze such speech attributes by transforming sound waves of the conversation between the user and provider into 2D, 3D, or holographic visual representation(s). Correlated image(s) or video of pupillary dilatation or constriction, degree of sweating, rate of eye blinking, eye movement, motor strength, balance, coordination, sensory perception, cranial nerves function, degree of alertness, ability to perform calculations, spatial correlations, higher executive brain functions as well as user/patient's temperature, heart rate, respiratory rate, tremors, fasciculations, quivering or other visual imageries of the user would be entered into pixel to pixel convoluted, recurrent or any neural network analyses of the unified image(s) data source(s). For example, the system may employ such speech/physical attributes to render predictive correlations related to "brain health." The system may generate other forms of indices, for example an "organ response to treatment" index, "organ disease burden" index, and "social burden" index. The "social burden" index can be an indicator of impact on family members, providers, or society as a whole. The system may generate, correlate, assess, and provide other types of indices related to organ health or the lack thereof.

Thus the present design may include an apparatus comprising a sensor configured to optically detect blood distribution analysis and spread at at least two external regions of a user via at least one of skin color, skin tone, skin temperature, skin condition, and capillary refill, and a processor configured to determine an image based on the optical detection of the sensor, the image indicating a first blood distribution and spread for a first region of the user and a second image indicating a second blood distribution and spread for a second region. The processor compares the first blood distribution and spread for the first region and the second blood distribution and spread for the second region to provide a blood-distribution/spread asymmetry representing a difference in heart health between the first region and the second region.

Blockchain Anonymization

The present device may employ anonymization in association with blockchain, anonymizing the information maintained thereon. In general, anonymization or deanonymization in the present design has similarities to the chromosomal DNA system, where DNA in humans is a double helix. The system employs a form of morphing based on nucleotide science, also referred to herein as genetic or DNA processing, mapping, or morphing. As used in this section, the term "system" may include the drone arrangement discussed, and/or the functions and components related to anonymization of data and placing and retrieving data to and from a distributed ledger arrangement, such as blockchain.

Each helix of chromosomal DNA is made of a "sugar-phosphate" backbone with "base pairs" for each double helix. A nucleotide is the basic structural unit and building block for DNA. These building blocks are hooked together to form a chain of DNA. A nucleotide is composed of three parts: five-sided sugar, phosphate group, and nitrogenous base (nitrogen containing).

The sugar and phosphate group make up the backbone of the DNA double helix, while the bases are located in the middle. A chemical bond between the phosphate group of one nucleotide and the sugar of a neighboring nucleotide holds the backbone together. Chemical bonds, i.e. (hydrogen bonds, between the bases across from one another hold the two strands of the double helix together. Four types of bases exist in DNA, namely Adenine (A), Cytosine (C), Guanine (G), and Thymine (T).

An allele is a variant form of a gene. Some genes have a variety of different forms, which are located at the same position, or genetic locus, on a chromosome. Humans are called diploid organisms because they have two alleles at each genetic locus, with one allele inherited from each parent. Each pair of alleles represents the genotype of a specific gene. Alleles contribute to the organism's phenotype, which is the outward appearance of the organism. Alleles may be dominant or recessive. Alleles can also refer to minor DNA sequence variations between alleles that do not necessarily influence the gene's phenotype.

The allele frequency represents the incidence of a gene variant in a population. Alleles are variant forms of a gene that are located at the same position, or genetic locus, on a chromosome. An allele frequency is the number of times the allele of interest is observed in a population divided by the total number of copies of all the alleles at that particular genetic locus in the population. Allele frequencies can be represented as a decimal, a percentage, or a fraction, and represent a numeric quantity of genetic diversity. Changes in allele frequencies over time can indicate that genetic drift is occurring or that new mutations have been introduced into the population.

In the present design, in one embodiment, the phosphate group may represent GPS location while the sugar group may represent time. The nucleotide bases represent the paired data points. For example, heart rate is paired with one or more relevant data points specific for that condition. For example, in a condition such as anemia, the two paired data points may be heart rate and hemoglobin count. Other alleles can exist pertinent to the same individual utilizing other relevant data points such as heart rate and mean corpuscular volume of red blood cells and so forth.

A nucleotide is the basic structural unit of human DNA and is formed of sugar-phosphate-nitrogenous base. In the present system, a nucleotide is equivalent to a codon, wherein a codon is constructed of a GPS-time-data point. These codons, or data codons, written on blockchain are anonymized. The system may employ deep machine learning and/or quantum computing methodology to predict the change between the actual reading and the predicted reading based on equations such as those shown in "Mathematical model for studying genetic variation in terms of restriction endonucleases," Nei et al., Proc. Natl. Acad. Sct. USA, Vol. 76, No. 10, pp. 5269-5273, October 1979, the entirety of which is incorporated herein by reference. As used herein, such processing is referred to as genetic or DNA processing of personal information scrubbed data.

In the present design, each codon starts with GPS-time, and then employs pertinent data point(s) with associated alphanumeric codes at predetermined intervals on the specific datasome, where a datasome is the ongoing sequential accumulation of different data codons. For example, a DNA sequence may be created, such as TCGTTATCAG . . . representing a genetic or DNA sequence, and that sequence applied to the data. The randomization of alphanumeric code happens on blockchain by customary and/or quantum computing. Two steps are employed in verification. First unlocking the "Geo-located" alphanumeric code on the desired datasome; second, pairing of codons. Morphing calls for by assigning random alphanumeric codes and/or code parts from other codons on other datasomes, like having parts of financial codons appended to or provided to a Health datasome, and so forth.

Assertive synchronization between different datasomes is authorized by the user via any of the agreed upon authorization methodologies available. An example is a user visiting a doctor, the doctor identifies the user using a Health Datasome (HD). The system morphs the user's HD, and additional blocks may be added in multiple dimensions by the doctor, and the user approves the changes to their HD. An assertive synchronization event is approved by the user between their HD and Financial Datasome (FD) for the doctor to be compensated and the system may further morph both HD and FD with a financial component, and the system saves the newly morphed Health Datasome Codon (HDC) and Financial Datasome Codon (FDC) on blockchain.

The user is identified by the doctor or other appropriate personnel before the visit via a de-anonymization process, authorized by the patient. At the end of the visit, the doctor or other appropriate personnel or entity generates a new data point with GPS and time stamps. The patient then approves the addition of a block or multiple blocks to his health datasome with the option of additional morphing of data points. For example, if he had a co-pay for the doctor's visit, he can use "fraction of cents" or "last four digits of credit card number" or any other piece of relevant financial information to "Morph" his Health codons for that visit. He can also morph it by relevant other information, e.g. fashion information like "what color shoes" he or she were wearing during the visit.

Authorization occurs to verify identity for the encounter and or addition of codons on one's datasome on blockchain, also authorization occurs to pay for goods and/or services. The system may employ public/private key technology to initiate the authorization process i.e. to obtain consent from the user to start the process of verification to receive the service, pay for service or goods, share de-identified information, add codons, morph codons and other data related processes pertaining to the individual.

Different data points may be employed in the system other than healthcare data points, such as diet, fitness, fashion, and nutrition.

The system of data anonymization employed herein may have multi-helices where the sugar-phosphate backbone is replaced by a "GPS-Time" backbone for the different datasomes, where a datasome is a chromosome of data employed in the current design. In the datasomes of the present design, "bases" are represented by the individual data point, such as vital signs and/or other health and medical related de-identified data points, co-localized with GPS location and time for the health datasome. The system performs de-anonymization after obtaining authorization from the user and can reveal personal identifiers, or simply the "pairing" of random data points similar to "base pairing," which can verify the concealed identity of that individual without revealing any personal identifiers. The system saves the de-identified data points pairing sequentially as a data footprint for the individual on a permissioned and/or permissionless blockchain. The system may use a few hundred or few thousand random data points for verification and distribution across the network, facilitating scaling.

The system converts, or morphs, collected data points into different distinctive structural formats that serve different functional roles. An example would be five different individuals with a heart rate of 90, representing an increased heart rate. One individual reaches a heart rate of 90 because of brisk walking, another individual had a heart rate lowering medication to bring heart rate down to 90, a third individual suffers from anemia causing him to have an elevated heart rate, a fourth individual lost some blood that caused his heart rate to be at 90, while the fifth individual became anxious and his heart rate reached 90. This shared single data point (heart rate 90) shared amongst all five individuals takes five distinctive three-dimensional structures that are different and totally exclusive for each one of those five individuals. If Global Positioning System (GPS) location, date and time stamps are added to such events, the situation exhibits a more unique identifier for each of these individuals as they uniquely exist in the space-time continuum without overlap. In the event that GPS localization fails to uniquely identify an individual, then the sequential GPS identifiers with date and time stamps can be used by the system, equivalent to the genomic sequence on a chromosome identifying an individual.

Thus different datasomes (data chromosomes) written to the blockchain are created to identify a user or individual, specific to certain circumstances, interactions and/or transactions. As examples, a "health datasome" (HD) can be used as an identifier for health interactions, a "sports datasome" (SD) can be used for sports interactions, a "nutritional datasome" (ND) can be used for nutritional interactions, a "financial datasome" (FD) can be used for financial interactions and so on and so forth. Each datasome carries an intrinsic "transactional value" written and reconciled on blockchain, either permissioned or permissionless. For example, a healthy individual having a certain intrinsic value, e.g. 10X in their HD and possibly less or more in their other datasomes depending on accrual systems employed.

In the present system, assertive synchronization between different datasomes is authorized by the user using a desired authorization methodology. An example would be a user visiting a doctor and the doctor identifying the user using HD, e.g. time of day, GPS location, etc. The system morphs the user's HD, and the system or doctor may add blocks in multiple dimensions. The user may approve changes to her HD. The user may approve an assertive synchronization event between her HD and PD for the doctor to get paid, for example, providing both healthcare and financial information together. The system may morph both HD and FD and the newly morphed HDC and FDC saved on blockchain. The system thus receives information related to a person, entity, transaction, morphs the information received a discussed below, and the morphed information is provided to blockchain, with the possibility of multiple morphings occurring in series or in parallel.

An example of a health datasome (HD) illustrates how datasomes are built on blockchain specific for the user and operation is similar for other datasomes (SD, ND, FD, etc.) using pertinent data points written on blockchain for each corresponding data codon (sequential coding blocks).

"Health datasomes" (HD) are encoded data sequences unique for any user, with a structure based on sequential coding of different elements, such as time (year, month, date, hour, minute, second), GPS coordinates (latitude, longitude and elevation), speed of the body of the user, human body anthropometric attributes (height, weight, eye color, hair color, body habitus, scars, moles, walking pattern, hand movements, certain facial gestures, etc.), human body vital signs of the user (including but not limited to: temperature, heart rate, blood pressure, respiratory rate, skin blood diffusion color, pupillary size, oxygen saturation, body weight, etc.), human body laboratory values of the user (including but not limited to blood glucose level, complete blood count, complete metabolic, hormonal, enzymatic and bacterial assays, etc.), human body radiological and/or radiographical findings (including but not limited to X-rays, CT scans, MRI, ultrasound, nuclear medicine, etc.), and human body disease symptoms and signs (including but not limited to: General: anorexia, weight loss, cachexia, chills and shivering, convulsions, deformity, discharge, dizziness/Vertigo, fatigue: malaise or asthenia, hypothermia, jaundice, muscle weakness, pyrexia, sweats, swelling, swollen or painful lymph node(s), weight gain, Cardiovascular: arrhythmia, bradycardia, chest pain, claudication, palpitations, tachycardia, Ear, Nose and Throat: dry mouth, epistaxis, halitosis, hearing loss, nasal discharge, otalgia, otorrhea, sore throat, toothache, tinnitus, trismus, Gastrointestinal: abdominal pain, bloating, belching, bleeding, constipation, diarrhea, dysphagia, dyspepsia, fecal incontinence, flatulence, heartburn, nausea, odynophagia, proctalgia *fugax*, pyrosis, Rectal tenesmus, steatorrhea, vomiting, Integumentary Hair: alopecia, hirsutism, hypertrichosis, Nail: clubbing, onycholysis, koilonychia, Skin: abrasion, anasarca, bleeding into the skin: petechia, purpura, ecchymosis and bruising, blister, edema, itching, Janeway lesions and Osler's node, laceration, rash, urticaria Neurological: abnormal posturing, acalculia, agnosia, alexia, amnesia, anomia, anosognosia, aphasia and apraxia, ataxia, cataplexy, confusion, dysarthria, dysdiadochokinesia, dysgraphia, hallucination, headache, akinesia, bradykinesia, akathisia, athetosis, ballismus, blepharospasm, chorea, dystonia, fasciculation, muscle cramps, myoclonus, opsoclonus, tic, tremor, insomnia, Lhermitte's sign, loss of consciousness, syncope, neck stiffness, opisthotonos, paralysis and paresis, paresthesia, prosopagnosia, somnolence, Obstetric/Gynecological: Last menstrual period, abnormal vaginal bleeding, amenorrhea, infertility, painful intercourse, pelvic pain, vaginal discharge, Ocular: amaurosis *fugax* and amaurosis, blurred vision, Dalrymple's sign, double vision, exophthalmos, mydriasis/miosis, nystagmus, Psychiatric: amusia, anhedonia, anxiety, apathy, confabulation, depression, delusion, euphoria, homicidal ideation, irritability, mania, paranoid ideation, phobia, suicidal ideation, Pulmonary: apnea and hypopnea, cough, dyspnea, hemoptysis, pleuritic chest pain, sputum production, Rheumatologic: arthralgia, back pain, sciatica, Urologic: dysuria, hematospermia, hematuria, impotence, polyuria, retrograde ejaculation, strangury, urethral discharge, urinary frequency, urinary incontinence and urinary retention, etc.)

The advantages of having separate datasomes as identifiers instead of personal identifiers such as name, age, address, social security number, driver's license number, etc. are in the area of privacy. Having separate identifiers using datasomes written in blockchain for different specific interactions further protects from quantum computing potential unraveling of securitized blockchain data blocks, hence the datasomes represent the overall topographic map without the nomenclature of the geography, making hacking or improper capture of such information virtually impossible, inhibiting identification of users without consent.

In the present blockchain arrangement, user identifiers/information are part of the individual account of the user. The user can grant access to any other user to show his account details.

The present design uses a key-pair (public/private), where the system attaches the key pair to every user account. If Yasir wants to see Bhaskar's information on the app, Yasir sends a request to Bhaskar to share the details. Yasir shares his public key with Bhaskar together with a request to allow information on this public key.

When Bhaskar allows access, he grants Yasir the ability to view account details, including HDs and other information on his account. User details are passed via API endpoint to the system server to provide the access information to the blockchain. Access request and approval are separate APIs. User details can be as simple as dictionary/json objects or as complex as randomized quantum computing methodology.

Thus third parties can access the anonymized data, such as via a secure node. Users can be offered incentives to provide access to user data, but in all instances the user is in control of releasing his or her data, or granting access, to third parties. The system may employ a data generator that decides if his/her data can be further released by the third party, such as in exchange for a benefit.

The system may use data aggregation techniques. The system may employ data aggregation in the data generator account in structured, unstructured or a combination format. The data generator may obtain 2D, 3D, or holographic data aggregating and converting tools to process and clean his/her data and convert such data from unstructured to structured or vice versa. The system can employ data generators to mine raw data for any specific reason, such as seeking to increase the value of the raw data. An example would be an unreported side effect of a pharmaceutical or chemical agent that can be negated by a certain action such as avoiding the sun or ingesting a certain food. Data generators may mine data related to the pharmaceutical or chemical agent and may make this determination or assessment, and certain third parties may potentially have an interest in such a finding.

The system may also perform real time data manipulation and prediction. Prediction models may be employed wherein data flow is set to accrue more data when available or provide real time access to data being collected and assessed. Such functionality may provide an ability to create and employ real time prediction models, either physiologic or pathologic, based on and for the generated data using any reasonable time frame, such as seconds, minutes, hours, days, weeks, months or years. The system may utilize or employ omissions of data or data manipulation in fine tuning the modeling in order to provide more accurate and realistic models.

The system may further employ third party data verification and securitization. The system may include a data generator that may refer to or employ third party verification of the raw data collected for quality control. One example is collecting body weight data from a scale for an obesity management program. The system data generator may subscribe to a third party data quality control program, such as via an API or an embedded tool in the scale used to weigh the patient, that assesses the quality of data generated and verifies the anonymized data is attributed to the same data generator without compromise of personal identifier information.

The system may also employ the accrual of data royalties. For an entity such as a healthcare provider or a fashion or cosmetic provider, the system may generate a care plan for a specific user need. Such care plan is specific to the care provider regardless of the raw data points the system uses to reach that proprietary care plan. If other providers or other third parties seek to use that proprietary output by the provider to train an artificial intelligence agent or for any other purpose, the provider can accrue points or royalty values or otherwise anonymously without revealing any personal identifiers. Different providers can aggregate their knowledge base and protect their collective information pertaining to care plans, designs, color combinations, fabrics, and so forth. Thus a third party provider seeking to obtain certain information may build up credit and may redeem that credit for anonymized information when authorized, where the information obtained contains no personal information.

The current system provides for unrestricted data ownership. Data generation is a primary requirement for data ownership under decentralized blockchain data management and banking processes using anonymized data. In other words, data generated is intended to be owned not by the underlying entities from which the data is collected, but rather the entity that collects and analyzes or otherwise processes the data. Ownership of data may be apportioned amongst users and providers based on agreed upon rules and regulations that may vary amongst user/providers communities. A record is kept on blockchain to anonymously trace data generation, as well as the transfer, lease, selling, acquisition or any other process related to anonymization of the underlying data.

Generated data are fully transactable and exchangeable with different cryptocurrencies, legal tender currencies and/or different rewards. Anonymized data can have different grades for the same class of data and value varies depending on free market conditions. The system may include a data exchange for different interested third parties to solicit anonymized data from data generators on blockchain. The value of a "block" of data on blockchain can vary based on certain attributes and market conditions.

In operation, user interaction with the device may entail the collection of data retained at the device, with data provided from modules to the device via WiFi, Bluetooth, or through a USB connection or by any other means known in the art. The processor at the device may process the data and may format the data into graphs, charts, diagrams, virtual assistants and other forms to be displayed to the user via, for example, the device (2D, 3D, or holographic) screen. The data and/or information may be controlled by the user and may be sent from the device, such as a drone, to a remote location, i.e. a virtual "cloud," where the information may be collected, analyzed, and/or stored. Once the system transmits user information to the remote devices, such user information may be maintained, analyzed, and specific user recommendations or information transmitted back to the user.

The system may provide varying levels of service. As one example, the system may provide a gold/silver/bronze level of service, wherein bronze is simply maintaining data at a remote site, silver is analyzing data and providing recommendations, and gold is a concierge type service where the user may be provided contact with available personnel (physicians, pharmacists, personal shoppers, cosmetics specialists, optometrists, dentists, etc.) and particular needs will be addressed. Different or alternate levels of service may be provided.

Figure 11:
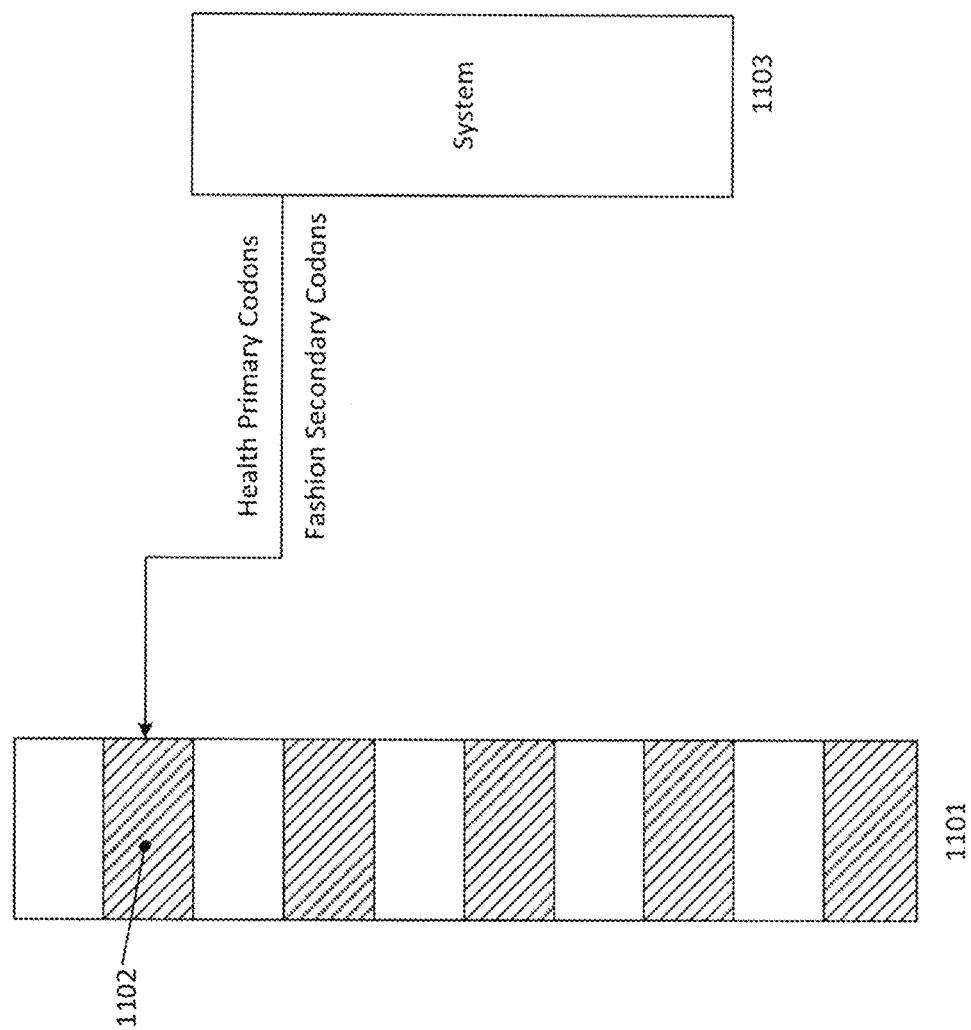
FIG. 11 illustrates a data locus as part of a health datasome.

The system may be generally understood according to the following Figures. FIG. 11 illustrates the concept of a data locus that is a data block on a distributed ledger system, such as blockchain, that includes multiple data codons. Health datasome 1101 is shown with data locus 1102, where data locus 1102 includes health primary codons and fashion secondary codons in this example. In this example, a patient/healthcare interaction occurs, which may be in person or not face to face, such as over the phone or internet. The system generates health primary codons and once approved, provides such codons to the blockchain. The Health datasome is combined or morphed with a secondary fashion codon on a specific data locus. As an example, the user may have an MRI and the results of the MRI may be combined or morphed by a specific fashion locus, which may be anything fashion related, such as what the user is wearing that day or a piece of clothing he identifies.

Figure 12:
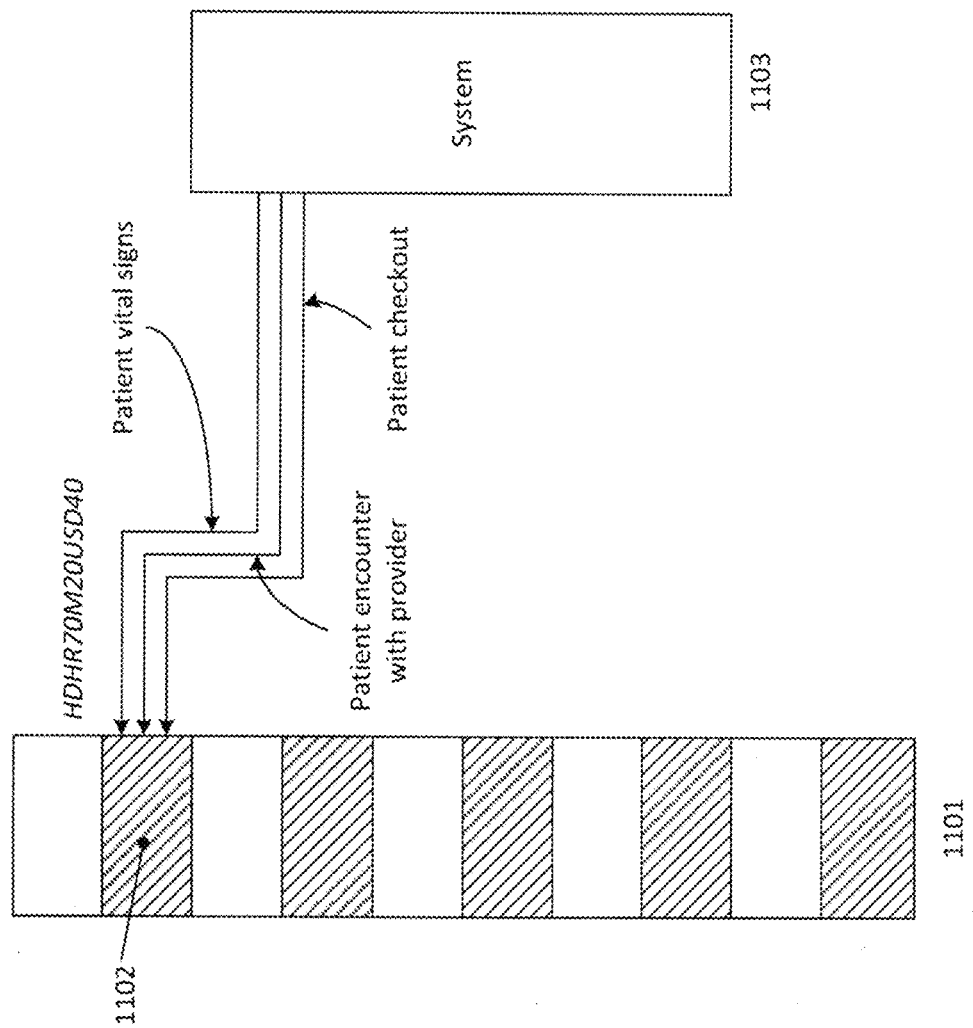
FIG. 12 shows data mapping to the health datasome.

FIG. 12 shows data mapping and nomenclature, wherein the system 1201 generates three sets of actions based on user-provider interaction. First, the system records user vital signs, second the system records the user's encounter with the healthcare provider, such as date, time, and GPS location of the encounter, and the system records the user's checking out from the encounter. The mapping of the region or encounter may be randomly established according to healthcare provider protocol, such as date, time, GPS location, examination room number, or otherwise, and the system may record attributes such as heart rate 70, 20 minute encounter on Tuesday Jan. 7, 2020 at 1:47 pm, and the system may assign a value equivalent, such as $40. Such a determination may be assigned by the healthcare provider with a value of HDHR70M20USD40, which may be further anonymized and processed or morphed using a secondary codon, such as fashion, and a blockchain hashtag. As shown in FIG. 12, the system 1103 then transmits the three pieces of information, anonymized and morphed, to blockchain including health datasome 1101 and data locus 1102. In this manner, the information is anonymized and randomized based on a provider or user provided piece of information. As a result, the user or provider may retain control of the information, only allowing de-anonymization at her or its pleasure.

Figure 13:
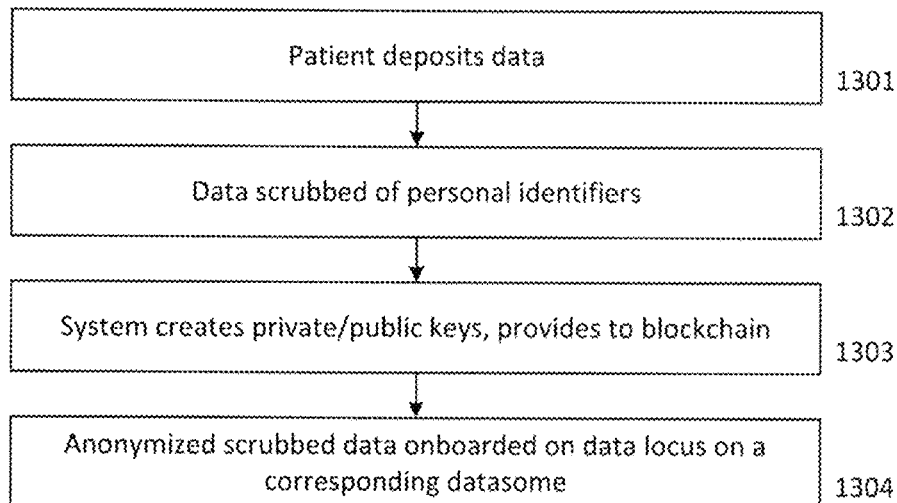
FIG. 13 is a flowchart representing anonymization of data provided.

FIG. 13 shows the general operation of anonymization of data. At point 1301, the user deposits data with the system. At point 1302 the system scrubs the data of personal identifiers, including but not limited to name and social security number. At point 1303, private and public keys are created for the entity having original control and those keys are provided to block chain. For a user retaining his test results, the user is typically the entity having original control. For a healthcare provider, such as a doctor or hospital, who creates data based on patient data, such as a report summarizing attributes of multiple patients, the healthcare provider may be the entity having original control of the report while the patient may have control of the underlying data. Keys are distributed accordingly at point 303. At point 304, the system places the anonymized scrubbed data on the data locus on a corresponding datasome.

Figure 14:
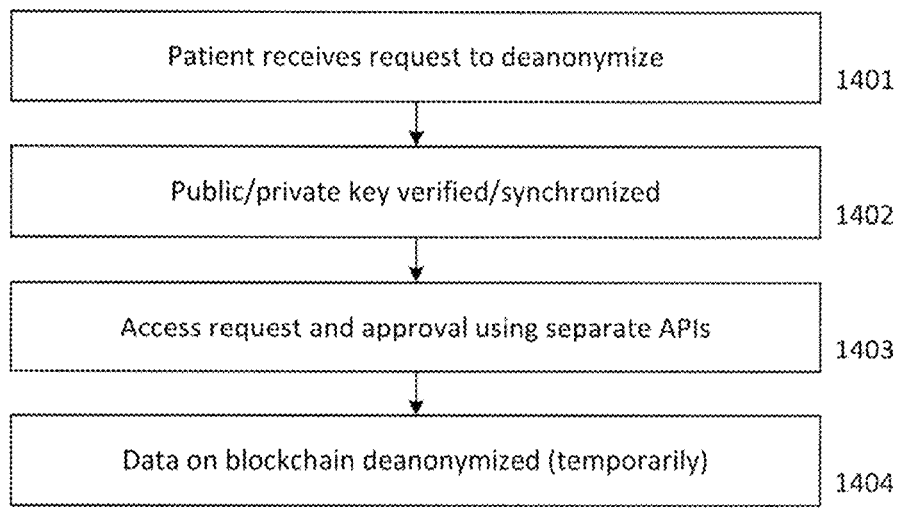
FIG. 14 is a flowchart illustrating deanonymization of data.

FIG. 14 illustrates deanonymization of data. From FIG. 14, the user receives a request to deanonymize data, via contact information for the user provided with the anonymized data. In general, the user may be assigned a unique identifier, typically by the system but possibly by the institution or even by the user, and this information may be selectively employed from the blockchain to provide a request to deanonymize data, and an entity requesting deanonymization may be provided. Such information is provided to a repository that correlates the unique identifier identifying the user with the current contact information of the user, which may be updated. As a very simple example, the healthcare facility may be assigned number 010101 while the patient my be assigned the number 1234, and thus the 0101011234 value may be provided to blockchain. When a request to deanonymize is provided by the system, the repository receives the request and contacts the user. Sufficient security to the repository is provided and in some instances may be provided on the blockchain. Point 1402 shows the system verifying and/or synchronizing public and private key information, an alternate method of verifying the user. Once the user, or entity holding the confidentiality, is contacted, the user may agree to access to the information, in one instance in exchange for value. Point 1403 calls for access request and approval using separate APIs for each. Once approved and access protocols are followed, the system deanonymizes the data and provides the data to the requestor at point 1404. Such anonymization and deanonymization can facilitate the transfer of monies as well as allowing access to care providers more readily than current methods. For example, if the user is injured in a remote location from her primary care physician, the physician at the remote location can request access and the user can provide access quickly and easily. Point 1404 deanonymizes and provides the information from the system to the approved requestor.

Figure 15:
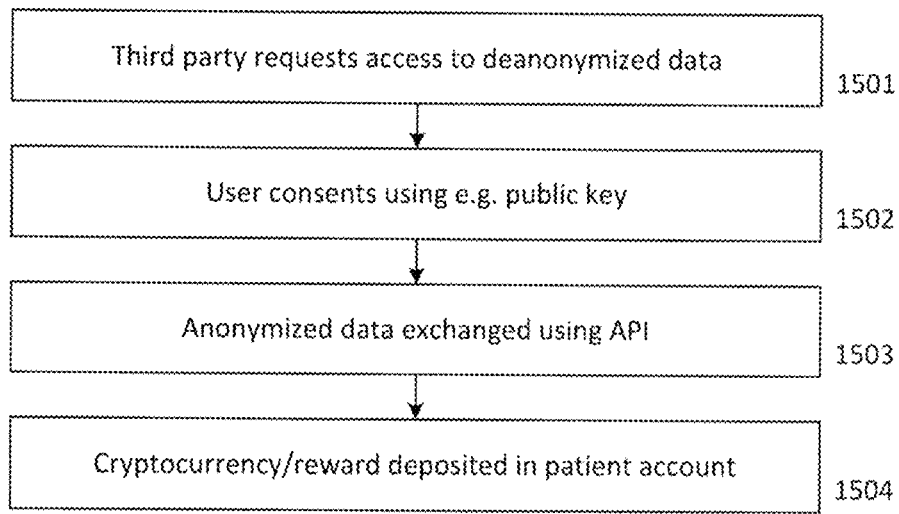
FIG. 15 shows the monetization of anonymized data.

FIG. 15 shows how such data can be assigned a value and the value exchanged for access to the data. At point 1501, a third party requests access to deanonymized data. The data may have a value preassigned to it, or the owner and requestor may negotiate, via the system, a value for exchange. At point 1502, the user consents using his public key only, but in this example not his private key. Consent may be provided in other ways, including via public and private key exchange, a system of approval and/or for entering negotiation, or otherwise. Once the requestor has been given the public key or other means of approval, the system provides anonymized data value, such as anonymized data points or monetary value, or some other thing of value from the requestor to the data holder via API at point 1503. At point 1504, the thing of value is provided to the entity holding rights in the data, i.e. the entity that approved the transaction for the value.

Figure 16:
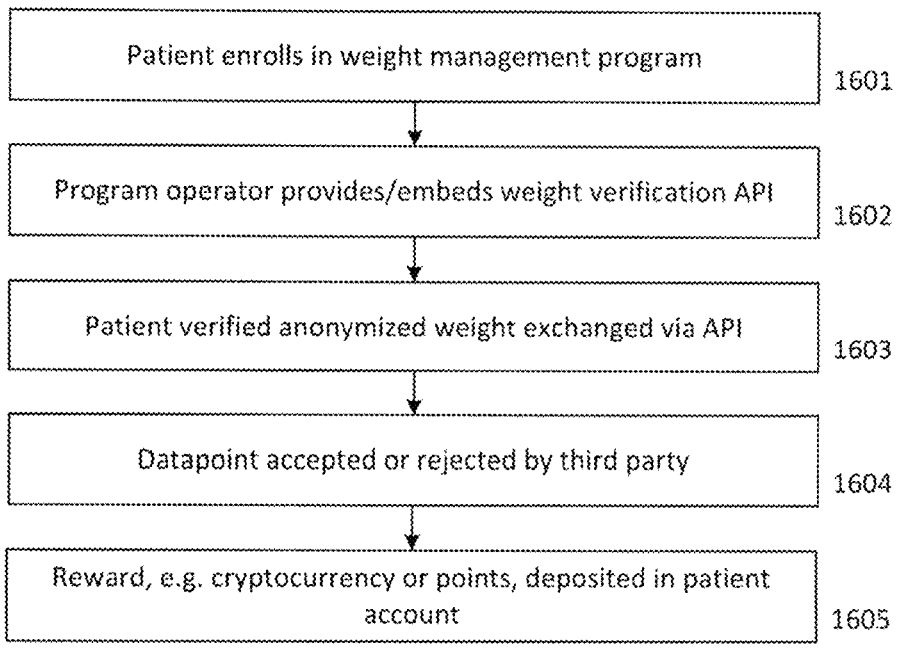
FIG. 16 is a flowchart of third party data verification.

FIG. 16 generally represents third party data point verification. The example of FIG. 16 involves a weight management program. At point 1601, the user enrolls in a weight management program. At point 1602, the program operator embeds a weight verification API. At point 1603, the system verifies an anonymous weight level is exchanged via API. At point 1604, the data point may be accepted or rejected by the third party, while at point 1605 the cryptocurrency or reward may be deposited into the patient's account. This provides an exchange of confidential information without compromising the confidential information and provides the user with an incentive to provide the confidential information.

Figure 17:
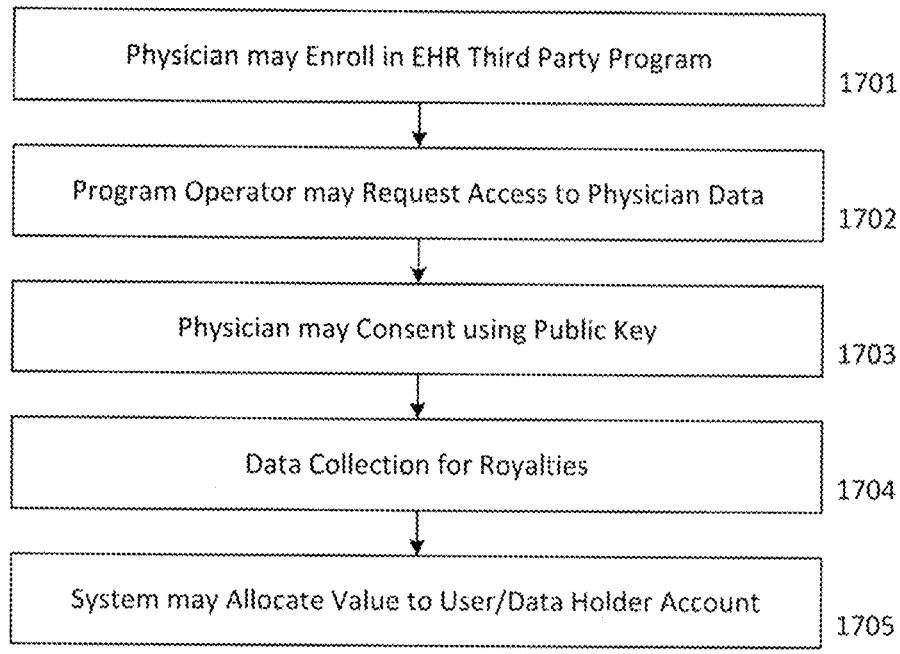
FIG. 17 shows accrual of anonymized data values, such as a royalty or reward.

FIG. 17 shows the accrual of loyalty points on the system. From FIG. 17, the physician may enroll in an EHR (Electronic Health Record) third party program at point 1701. At point 1702, the program operator may request access to the physician's data. At point 1703, the physician may consent using her public key, while at point 1704 data collection for royalties occurs, where the data collection includes anonymized data. At point 1705, the system may allocate value, such as cryptocurrency, points, or currency or some other reward, to the user or data holder's account. In this manner, the physician can provide data and additional data can be sought using incentivization, thus providing significant amounts of data as desired and obtainable.

Figure 18:
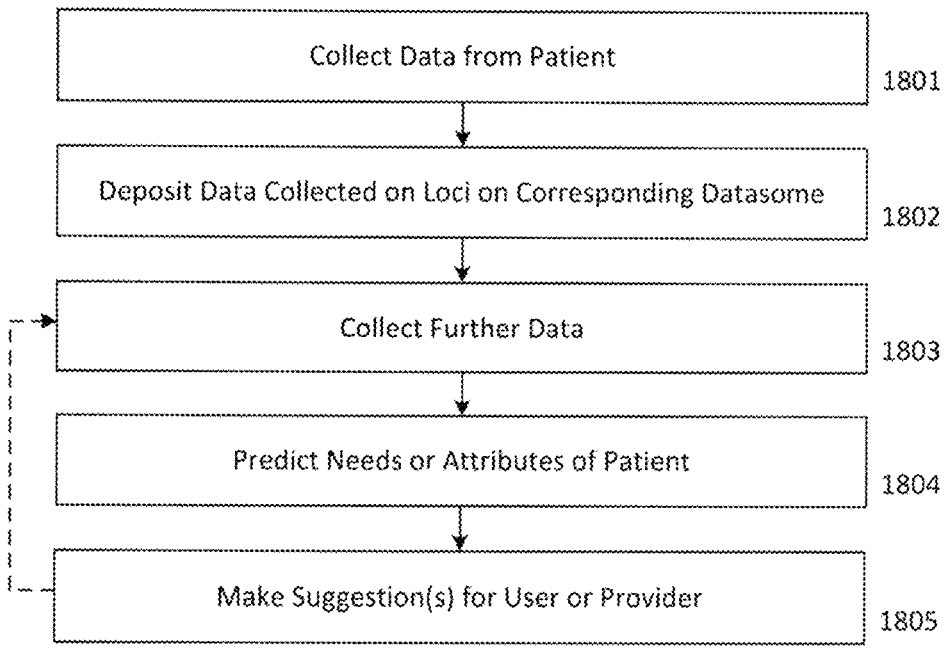
FIG. 18 is a flowchart of anonymized data point collection.

FIG. 18 shows anonymized data point collection, wherein at point 1801, mirror, display device, handheld unit, drone, peripheral, contactless evaluation device, or other device collects data from the patient. At point 1802, the system deposits the data collected on loci on a corresponding datasome. Point 1803 shows the example of an interactive diary interacting with an AI agent or human to collect further data, such as the food the patient is eating, the exercise the patient is getting, and so forth. Point 1804 is a general prediction loop, seeking to predict needs or attributes of the patient, where the data prediction loop in one instance is a reciprocal user-provider data prediction loop. Such a data prediction loop seeks for the system to predict a need or an action by the user, such as a desired action, and providing that action to the user, whereupon the user may accept the need or perform the action, and may inform the system. The system may then make a further prediction, such as the user is ignoring the suggestion to ride his bicycle, so instead the system recommends decreasing food intake or a different form of exercise. Positive feedback and encouragement or points or a thing of value may be provided to incentivize the user. Point 1805 calls for the system to make at least one suggestion for the user or provider, and an optional feedback path is shown.

Figure 19:
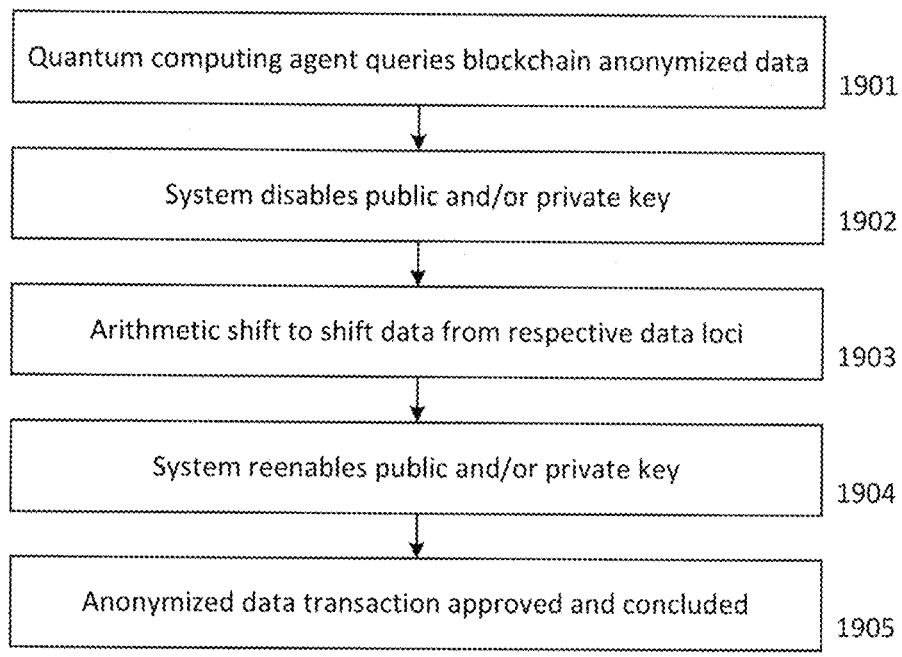
FIG. 19 is a flowchart of an arithmetic shift to safeguard against quantum computing hacking.

FIG. 19 illustrates a blockchain anonymized data arithmetic shift to safeguard against intrusion or hacking. From FIG. 19, the system employs a quantum computing agent that queries blockchain anonymized data at point 1901. At point 1902, the system disables public and private key functionality. Point 1903 calls for the system to employ arithmetic shift to shift data from their respective data loci, while point 1904 reenables public and private key functionality. Point 1905 approves and concludes the anonymized data transaction.

Figure 20:
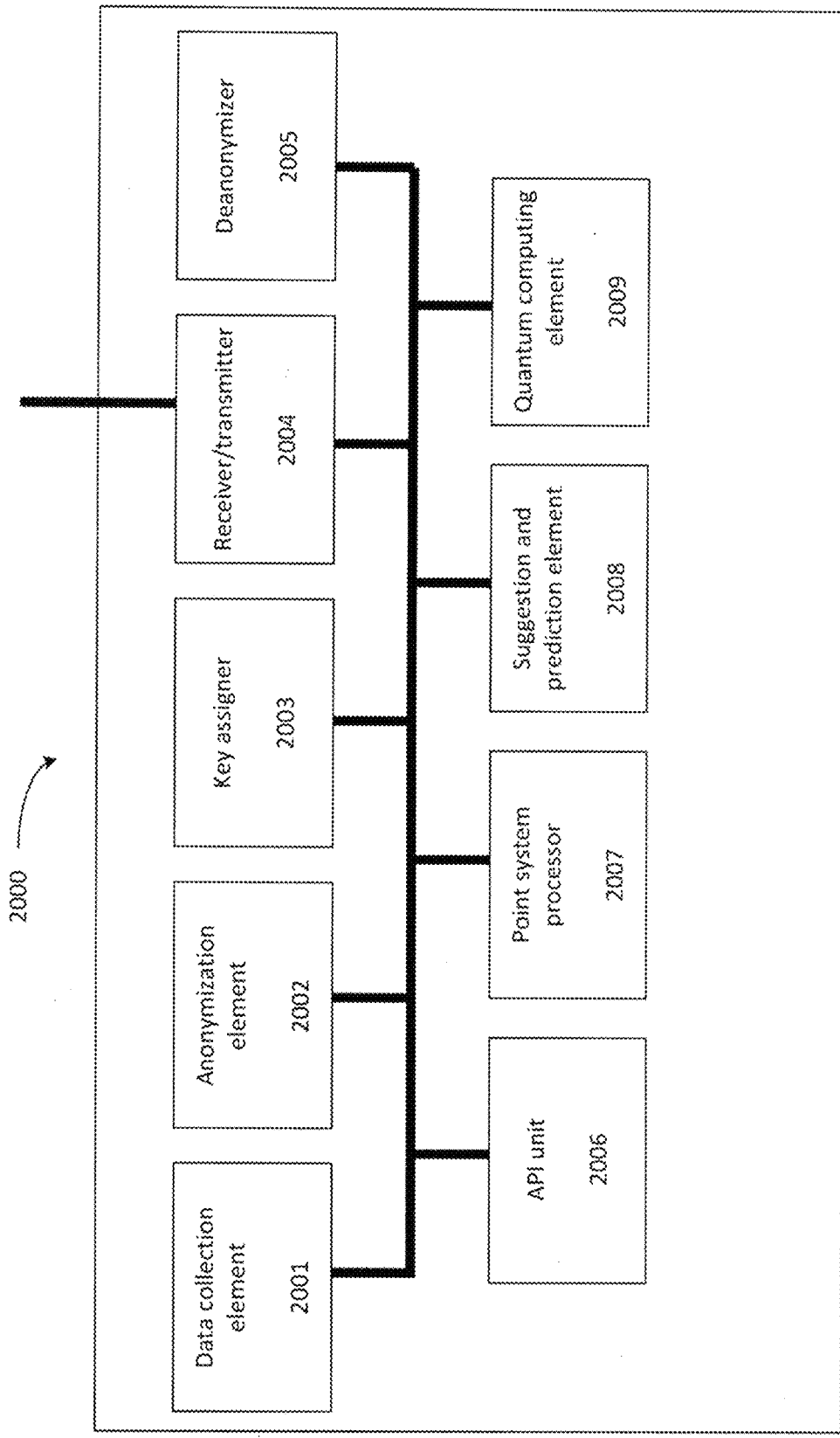
FIG. 20 is a general overview of an embodiment of the present design.

FIG. 20 is a general overview of the blockchain system including the functionality discussed. FIG. 20 may employ a combination of hardware and software but the functionality represented may be employed. Less or more than is shown in FIG. 20 may be employed in a system according to the current teachings, and some of the functionality may be provided on different components or at different locations. From FIG. 20, there is provided system 2000, including a data collection element 2001 that may collect data in any form via receiver/transmitter 2004. Data collection element 2001 may provide data to anonymization element 2002 which anonymizes the data, such as according to the genetic anonymization discussed herein. Anonymization element may scrub the information of personal data. Key assigner 2003 assigns public and private keys, and receiver/transmitter 2004 transmits the anonymized data to blockchain or appropriate public or private distributed ledger arrangement.

Deanonymizer 2005 receives a user request to deanonymize data and employs key assigner 2003 or other appropriate key verification objects to synchronize or verify key attributes. Again, public and private keys are discussed here, but other security measures may be provided to verify the entity requesting deanonymization. API unit 2006 provides necessary APIs for incoming and outgoing processing. Point system processor 2007 is shown to provide ability for the user to obtain value for allowing access to the information, whether by points, cryptocurrencies, or other items of value. Point system processor 2007 may perform at least some of the functionality show in in FIGS. 16 through 18, including offering an ability to negotiate value, to award points for permitting access to data, searching for additional data when requested, and so forth. Suggestion and prediction element 2008 provides for providing the user with suggestions based on individual performance and needs of the patient in question. Quantum computing element 2009 performs the functionality of FIG. 19.

Figure 21:
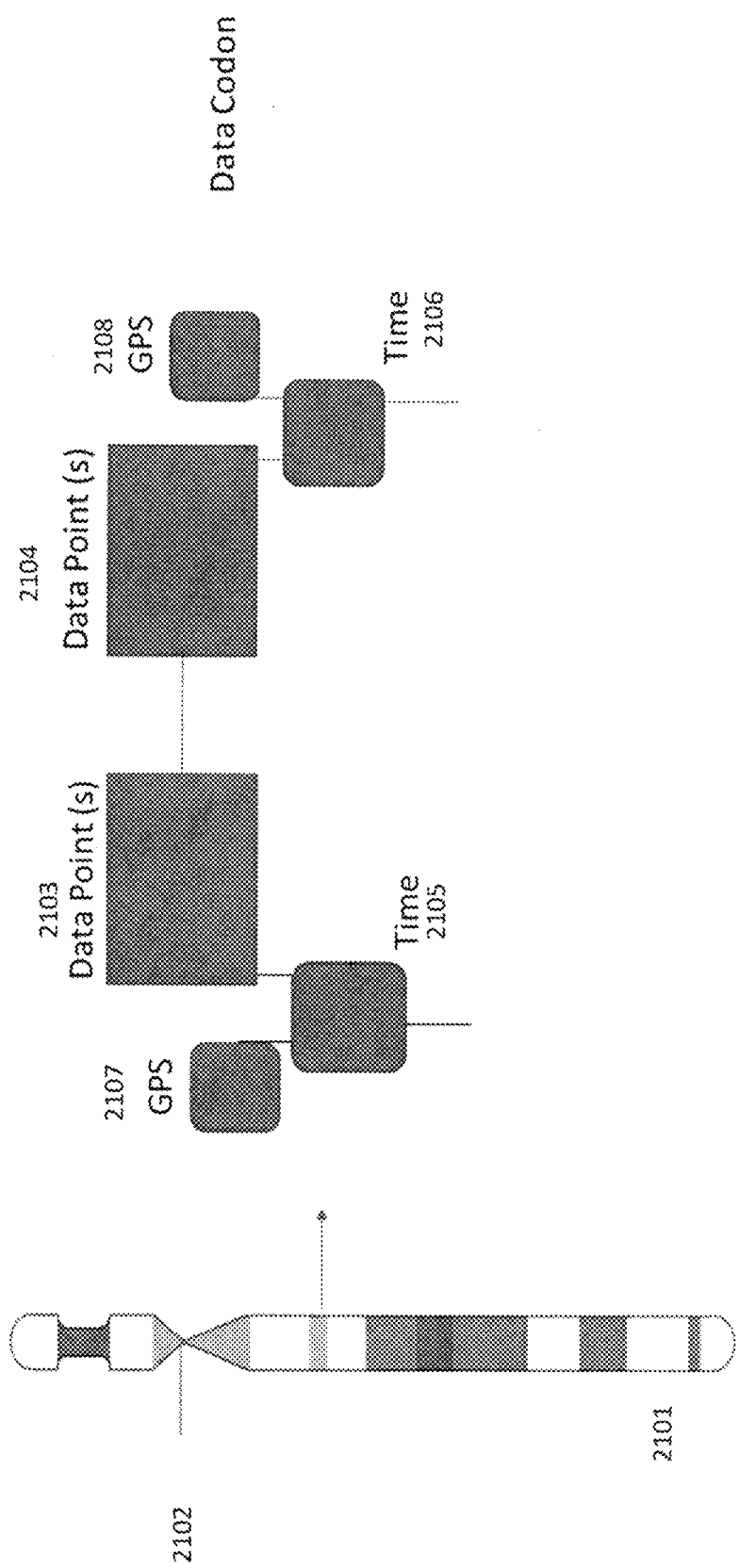
FIG. 21 shows a codon, the basic structure of a datasome, and the construction of a codon.

FIG. 21 shows a codon, the basic structure of a datasome, and the construction of a codon. The codon is made of co-localized and co-registered general and specific data points relevant to the datasome in question. General data points may include but are not limited to time (date: year, month, day, timestamp: hour, minute, seconds, milliseconds), GPS location (longitude, latitude and height or altitude), Device ID, and so forth. Specific data points for a health datasome (HD) include vital signs, symptoms, medications, lab tests, radiology tests, and so forth, expressed in a known manner, such as an alphanumeric manner. The system can co-register or co-localize data among specific and/or general data points. An example of this is to collocate two examinations, or two sets of examination results, or two sets of attributes such as results of a medical examination collocated with a fashion preference.

The system can also perform a morphing of datasomes, generally a processing that alters the datasome when being applied to the distributed ledger system or blockchain. In one instance, a shape can be provided making the datasome easier to identify, wherein the system applies three dimensional or two dimensional morphing of the datasomes into or using shapes, figures or other demarcating features to securitize the data blocks created on the datasome and/or facilitate retrieval of anonymized data by one with access to the the user or third party. One example of morphing shown in FIG. 21 is to provide the data in an "hourglass" shape, associating in this case fashion data with a specific locus on a health datasome, providing additional securitization of the anonymized data, or to make it easier for the user or a third party to identify and/or retrieve the anonymized data. In this example, the hourglass shape indicates to a viewer that the information, anonymized, is associated with a healthcare entry combined with a fashion entry. Another example of morphing would be to combine the data with a visual representation, such as a visual representation of broccoli, relating intentionally to a data locus on the health datasome where the user took his blood pressure measurement and blood pressure medication and a third party, such as a pharmaceutical company, is interested in the relationship of broccoli to a blood pressure medicine in question and employed by the patient.

The right side of FIG. 21 shows the general assembly and morphing of information. Couple this with genetic or DNA processing, wherein the underlying data is imposed on a genetic or DNA chromosome, such that the result is something like GCTATTGCT etc., and the result is an increase in security. FIG. 21 shows on the left a 3D morphed health datasome 2101 that may be put on a distributed ledger system and that may be viewed by parties having access, wherein point 2102 is a fashion morphing indication that provides an "hourglass" appearance and shape to the underling data. A party reviewing may be able to understand that an hourglass shape of this type means healthcare data morphed with fashion data. Colors, visual representations, different shapes, and so forth may represent different underlying data. FIG. 21 on the right shows a healthcare data point 2103, a time 2105, and a GPS location 2107, and this may be augmented with additional or different data, e.g. device ID, etc. On the right side is a fashion data point or may be any other information, including a second healthcare datapoint taken at a different time, even in the same visit. The two may be combined together, the information coded and genetically or DNA mapped, and provided to the distributed ledger. Data point or points 2104 may be provided with time 2106 and GPS location 2108, wherein the combined information forms a data codon.

Figure 22:
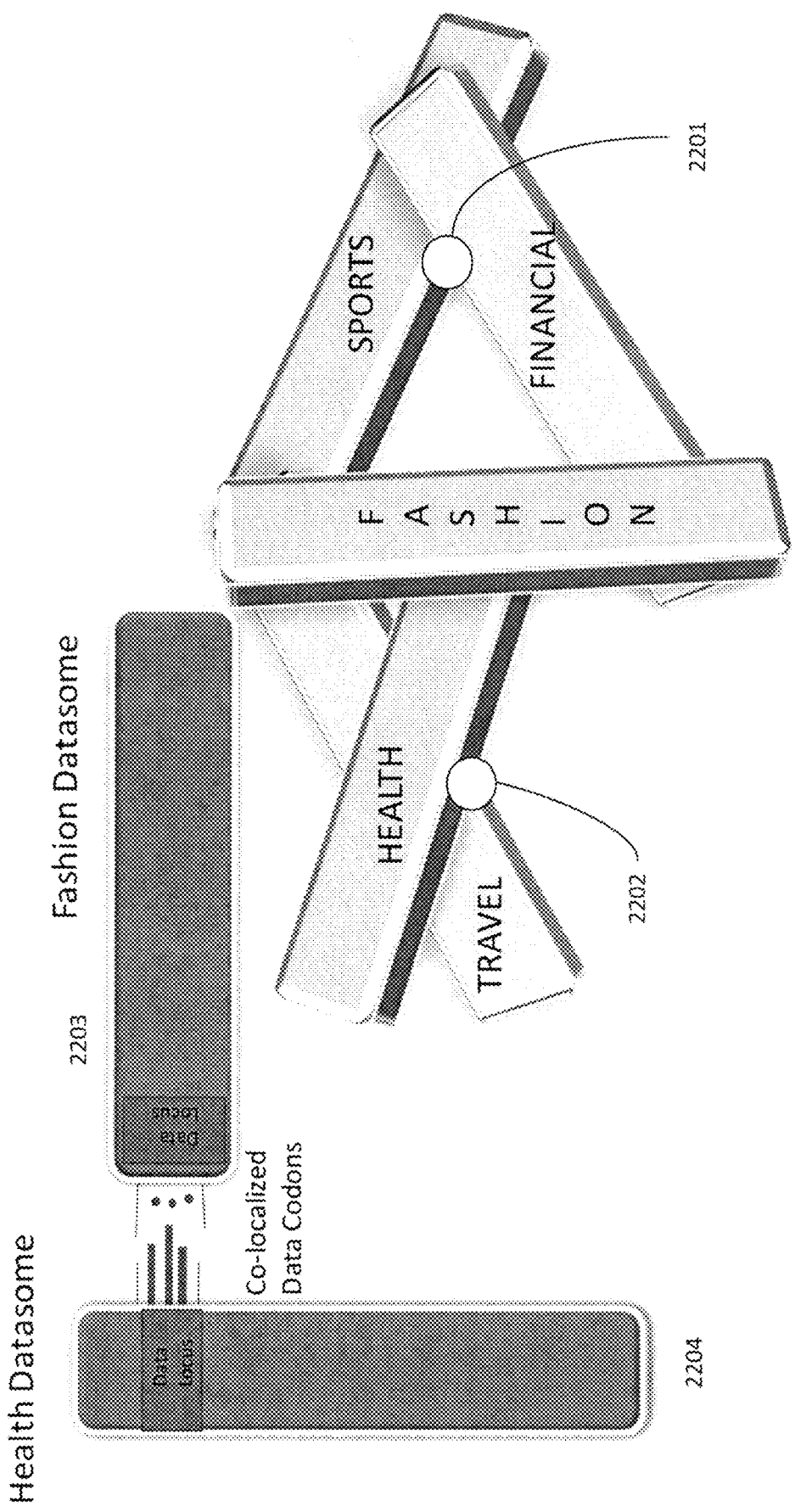
FIG. 22 shows relationships between datasomes and parts of datasomes conceptually.

FIG. 22 is a generalized representation of the intersection between various concepts used to determine datasomes. On the right, point 2201 represents the intersection between sports and financial, such that a datasome may contain sports and financial information, while point 2202 represents an intersection between health and travel. The combined information can serve to further securitize the underlying information. The left side of FIG. 22 shows a fashion datasome 2203 with three points being co-localized, such as is shown on the right side of FIG. 21, where the co-localized data codons of the fashion datasome are provided to the health datasome 2204. This provides combined data, again having an enhanced tendency to limit security breaches.

Figure 23:
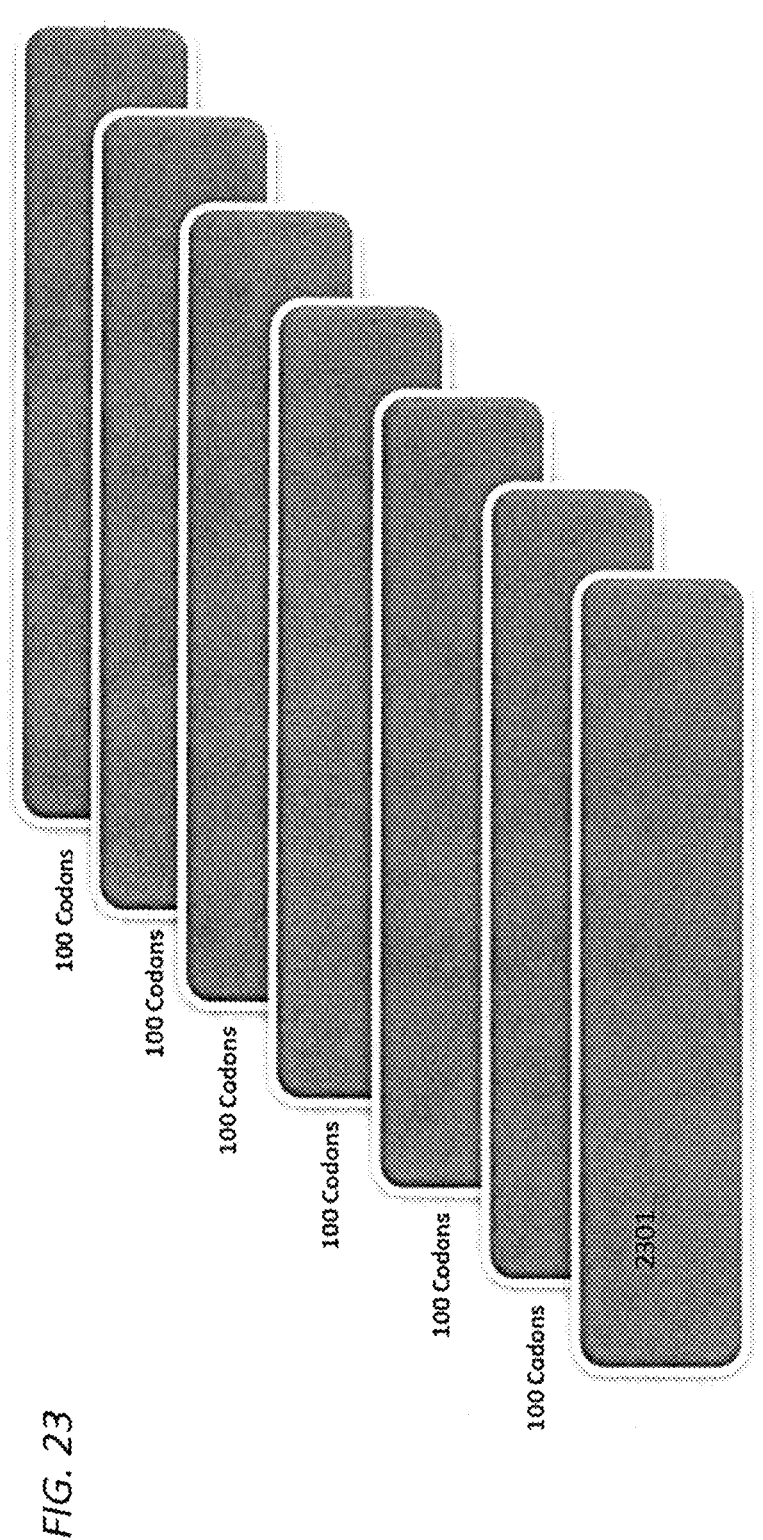
FIG. 23 shows the general concept of prediction, such as by using a generative adversarial network (GAN).

FIG. 23 shows one form of prediction employed by the system. Codons may be formed by the system, representing a prediction, such as a prediction that patient X will have a blood clot based on existing known information about patient X. The system may employ a corrective generative adversarial network (GAN) using deep machine learning and/or quantum computing methodology, in essence two or more neural networks that contest with each other in a game that is corrected and re-calibrated with real world scenarios. Such a generative network may generate candidates that are evaluated using a discriminative network. Codons, or codon groups such as 100 codon group 2301, may be developed by the system, and multiple such codons or codon groups may be developed. When operating a contest, the system operates based on data distributions. Typically, the generative network learns to map from a latent space to a data distribution of interest, while the discriminative network distinguishes candidates produced by the generator from the true data distribution. The generative network's training objective is to increase the error rate of the discriminative network, or in other words, to the GAN produces novel candidates that the discriminator network believes are not synthesized but instead are part of the true data distribution. As an example, in healthcare, the system may conduct a "game" on physiological and pathological virtual twins using anonymized data. The system alters and recalibrates resultant predictions about the virtual twins and generates suggestions to the patient/user and/or provider, and the system may improve predictions over time based on additional data and further processing. For example, if persons exhibiting characteristic X are believed to have an 87% chance of developing condition Y, and data suggests or the network determines the number has decreased to 83%, that number may be provided. Thus according to the present design, a real time prediction model may be provided that computes the probability of formation of a new codon under the assumption of random codon distribution and co-localization, and the system may develop and assess a new codon or codons for purposes of improving predictions.

Sports Applications

In another embodiment related to the field of sports medicine and sports technology, providing "on the field" evaluation and management of sports injury and/or player susceptibility to an injury may be beneficial. The present design may also include a field side charging station wherein a drone or drones can be placed near the field of play to be deployed for contactless evaluation and management of on-field sports injuries or just following certain contactless parameters pertaining to fitness parameters of a certain sport. Such contactless parameters may include, but are not limited to, speed, agility, technique, vigor, exertion and susceptibility and prediction of injury during training. The drone can monitor activity and in certain instances may be deployed in response to a gesture by a player, trainer or any other team member, or a processing device may be employed to release the drone, such as a device wherein when a signal is provided the drone is released. Such a signal may be provided by a third party or an automated artificial intelligent agent, which may be considered a deployment device. The deployment device can gather pertinent information using sensor(s), and functions may vary and may depend on what is required. As may be appreciated, any list of functions may be changed, improved, reduced, or otherwise altered depending on a variety of factors, including but not limited to popularity of the functions, needs and desires expressed by users, use patterns, costs associated with apps and functions, and so forth. Certain functions may be provided either locally, i.e. at the device, or remotely, i.e. at the remote device arrangement, or a combination of both. In general, the system, including the device and remote device arrangement, receive information and queries and respond appropriately for sports issues that arise.

Examples of the determinations made and functions provided are as follows. In the area of health, lung health may be maintained and monitored, and the device may determine respiratory rate (RR), $CO_2$ level, lung volume, pulse oximetry, breathing characteristics, jugular vein distension (JVD), edema. The device may respond with a chart including a degree of hypoxia, a graph with the user's lung volume as compared to users of similar age and sex, and a pitting edema score. In the area of heart health, the device may collect pulse/heart rate, blood pressure, heart rhythm, and EKG values with appropriate modules. The device may determine and/or report a graph, raw data, and or percentile data, as well as recommendations. In the field of eye health, the system may assess or determine sclera color, visual acuity, peripheral vision, analyze the pupil, iris, sclera, and so forth, determine eye pressure, redness or dryness, and eyelash evenness, and the system may provide a digital model of the eye, a scoring of quantities such as peripheral vision, raw data, percentile values, a chart, and a chart or graph.

Many, if not all, of the health related evaluations may result in a combination of a score or scores, raw data, percentile, and a chart or graph of the health of the particular site. These and other relevant information (recommendations, warnings, pictures, etc.) may be determined and provided as appropriate, but the system may make and provide all such determinations when assessing health parameters.

The system may assess spine health according to structures or deformities, warmth, swelling, range of motion (ROM), presence of scoliosis, and gait. The system may assess joint health by evaluating warmth to the area, ROM, swelling, presence of nodules, and/or gait. The system may assess skin health according to skin turgor, color, skin breakdown, blood perfusion and degree of edema. The system may assess foot health by collecting signs of infection, color, hair distribution, skin integrity, and degree of pitting or edema. In addition to the other reporting data, the system may provide a digital model of feet or the lower extremities and may provide digital models of other body parts as appropriate.

Another embodiment pertains to over all hospitals and healthcare facilities workflow. A healthcare facility clerk typically manages the medical and non-medical requests of patients and their families simultaneously and/or sequentially. The system may include a central operator and/or artificial intelligence agent residing in for example, a patient's room. Such a central operator may engage with components provided in the patient's room and can simultaneously and/or sequentially deploy a drone to a room or nurse's station to collect samples, deliver pharmaceutical agents, nutritional products, magazines, or other products, goods and/or services.

In operation, user interaction with the device may entail the collection of data retained at the device, with data provided from modules to the device via WiFi, Bluetooth, or through a USB connection or by any other means known in the art. The processor at the device may process the data and may format the data into graphs, charts, diagrams, virtual assistants and other forms to be displayed to the user via, for example, the device (2D, 3D, or holographic) screen. The data and/or information may be controlled by the user and may be sent from the device, such as a drone, to a remote location, i.e. a virtual "cloud," where the information may be collected, analyzed, and/or stored. Once the system transmits user information to the remote devices, such user information may be maintained, analyzed, and specific user recommendations or information transmitted back to the user.

The system may provide varying levels of service. As one example, the system may provide a gold/silver/bronze level of service, wherein bronze is simply maintaining data at a remote site, silver is analyzing data and providing recommendations, and gold is a concierge type service where the user may be provided contact with available personnel (physicians, pharmacists, personal shoppers, cosmetics specialists, optometrists, dentists, etc.) and particular needs will be addressed. Different or alternate levels of service may be provided.

Thus according to one embodiment of the present design, there is provided a system comprising a drone device comprising a plurality of securable compartments, each of the securable compartments lockable and configured to be unlocked by a user or a remote device, wherein the user comprises a user approved to unlock at least one locking compartment, a series of sensors provided with the drone device and configured to assess health attributes of the user while the drone is positioned proximate the user, and a remote computing system configured to receive sensed information from the drone device and assess health of the user, wherein the remote computing system holographically displays health attributes of the user. The drone device travels to the user to provide or receive healthcare related objects to or from the user, and the series of sensors comprise at least one audio sensor and at least one video sensor jointly configured to assess user health attributes about the user's body in a contactless manner based on both audio and visual health attribute readings, wherein the contactless manner comprises refraining from physically contacting the user's body.

According to another embodiment of the present design, there is provided a rechargeable drone device arrangement comprising a series of sensors configured to receive information about a user and transmit the information to a computing system configured to assess the information collected from the drone device, a plurality of locking securable compartments configured to maintain samples or medications, wherein the plurality of locking securable compartments are each configured to be openable only by an approved individual, and a remote computing system configured to receive sensed information from the drone device and assess health of the user, wherein the remote computing system holographically displays health attributes of the user. The drone device travels to the user to provide or receive healthcare related objects to or from the user. The series of sensors comprise at least one audio sensor and at least one video sensor jointly configured to assess user health attributes about the user's body in a contactless manner using both audio and visual health attribute readings, wherein the contactless manner comprises refraining from physically contacting the user's body.

According to a further embodiment of the present design, there is provided a system comprising a drone device comprising a plurality of locking securable compartments, each of the plurality of locking securable compartments configured to be unlocked only by a user or a remote device, wherein the user comprises a user approved to unlock at least one locking securable compartment, and a series of sensors configured to assess health attributes of the user while the drone is positioned proximate the user, wherein the series of sensors comprise at least one audio sensor and at least one video sensor configured to assess user health attributes about the user's body in a contactless manner based on both audio and visual health attribute readings, wherein the contactless manner comprises refraining from physically contacting the user's body, and a remote computing system configured to receive sensed information from the drone device and assess health of the user, wherein the remote computing system holographically displays health attributes of the user. The drone device travels to the user to provide or receive healthcare related objects to or from the user.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A system comprising:
a drone device comprising a plurality of securable compartments, each of the securable compartments lockable and configured to be unlocked by a user or a remote device, wherein the user comprises a user approved to unlock at least one locking compartment;
a series of sensors provided with the drone device and configured to assess health attributes of the user while the drone is positioned proximate the user; and
a remote computing system configured to receive sensed information from the drone device and assess health of the user, wherein the remote computing system holographically displays health attributes of the user;
wherein the drone device travels to the user to provide or receive healthcare related objects to or from the user;
wherein the series of sensors comprise at least one audio sensor and at least one video sensor jointly configured to assess user health attributes about the user's body in a contactless manner based on both audio and visual health attribute readings, wherein the contactless manner comprises refraining from physically contacting the user's body.

2. The system of claim 1, wherein the apparatus further comprises a charging station used to electrically recharge the drone device.

3. The system of claim 1, further comprising a transport mechanism configured to maintain and transport the drone device to a desired location and deploy the drone toward the user.

4. The system of claim 1, wherein the plurality of securable compartments are each configured to maintain at least one medication for the user.

5. The system of claim 1, wherein the plurality of securable compartments are each configured to receive samples provided by the user or a healthcare individual.

6. The system of claim 1, wherein the series of sensors comprise a camera sensor.

7. The system of claim 1, wherein the series of sensors comprise a microphone.

8. A rechargeable drone device arrangement comprising:
a series of sensors configured to receive information about a user and transmit the information to a computing system configured to assess the information collected from the drone device;
a plurality of locking securable compartments configured to maintain samples or medications, wherein the plurality of locking securable compartments are each configured to be openable only by an approved individual; and
a remote computing system configured to receive sensed information from the drone device and assess health of the user, wherein the remote computing system holographically displays health attributes of the user;
wherein the drone device travels to the user to provide or receive healthcare related objects to or from the user;
wherein the series of sensors comprise at least one audio sensor and at least one video sensor jointly configured to assess user health attributes about the user's body in a contactless manner using both audio and visual health attribute readings, wherein the contactless manner comprises refraining from physically contacting the user's body.

9. The rechargeable drone device arrangement of claim 8, wherein the rechargeable drone device is further configured to engage a charging station that electrically recharges the rechargeable drone device.

10. The rechargeable drone device arrangement of claim 8, wherein the drone device is configured to be provided to a transport mechanism configured to maintain and transport the rechargeable drone device to a desired location and deploy the rechargeable drone device toward the user.

11. The rechargeable drone device arrangement of claim 8, wherein the plurality of locking securable compartments are each configured to maintain at least one medication for the user.

12. The rechargeable drone device arrangement of claim 8, wherein the plurality of locking securable compartments are each configured to receive samples provided by the user or a healthcare individual.

13. The rechargeable drone device arrangement of claim 8, wherein the series of sensors comprise a camera sensor.

14. The rechargeable drone device arrangement of claim 8, wherein the series of sensors comprise a microphone.

15. A system comprising:
   a drone device comprising
      a plurality of locking securable compartments, each of the plurality of locking securable compartments configured to be unlocked only by a user or a remote device, wherein the user comprises a user approved to unlock at least one locking securable compartment; and
      a series of sensors configured to assess health attributes of the user while the drone is positioned proximate the user, wherein the series of sensors comprise at least one audio sensor and at least one video sensor configured to assess user health attributes about the user's body in a contactless manner based on both audio and visual health attribute readings, wherein the contactless manner comprises refraining from physically contacting the user's body; and
   a remote computing system configured to receive sensed information from the drone device and assess health of the user, wherein the remote computing system holographically displays health attributes of the user;
   wherein the drone device travels to the user to provide or receive healthcare related objects to or from the user.

16. The system of claim 15, further comprising a transport mechanism configured to maintain and transport the drone device to the position within travel distance of the user and deploy the drone toward the user.

17. The system of claim 15, wherein the plurality of locking securable compartments are each configured to maintain at least one medication for the user.

18. The system of claim 15, wherein the plurality of locking securable compartments are each configured to receive samples provided by the user or a healthcare individual.

19. The system of claim 15, wherein the series of sensors comprise a camera sensor.

20. The system of claim 15, wherein the series of sensors comprise a microphone.

* * * * *